(12) United States Patent
Tajima

(10) Patent No.: US 6,455,325 B1
(45) Date of Patent: *Sep. 24, 2002

(54) LIQUID PROCESSING METHOD MAKING USE OF PIPETTE DEVICE AND APPARATUS FOR SAME

(75) Inventor: Hideji Tajima, Tokyo (JP)

(73) Assignee: Precision System Science Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,488

(22) Filed: Feb. 3, 1999

Related U.S. Application Data

(63) Continuation of application No. 08/737,946, filed on Nov. 20, 1996, now Pat. No. 5,895,631.

(30) Foreign Application Priority Data

Mar. 20, 1995 (JP) ............................................. 7-086005
Mar. 19, 1996 (JP) ............................................. 8-089050

(51) Int. Cl.[7] ........................ G01N 35/553; B01L 3/02
(52) U.S. Cl. ................ 436/526; 422/100; 436/525; 435/286.4; 435/286.5; 435/287.7; 435/287.8; 435/309.1
(58) Field of Search ............................. 422/101, 100; 436/526, 525; 435/286.4, 286.5, 287.7, 287.8, 309.1

(56) References Cited

U.S. PATENT DOCUMENTS 3,985,649 A * 10/1976 Eddelman .................. 210/42
4,275,591 A * 6/1981 Wand ...................... 73/864.16
4,292,920 A * 10/1981 Smith et al. ................ 118/425
4,526,046 A * 7/1985 Oberli ..................... 73/864.16
4,895,650 A * 1/1990 Wang ........................ 210/222

(List continued on next page.)

FOREIGN PATENT DOCUMENTS

| | | |
|---|---|---|
| AU | A-72820/94 | 3/1995 |
| EP | 0 676 643 A2 | 10/1995 |
| JP | 2-161358 | 6/1990 |
| JP | 2-242161 | 9/1990 |
| JP | 4-357460 | 12/1992 |
| JP | 5-256859 | 10/1993 |
| JP | 6-109741 | 4/1994 |
| JP | 6-160401 | 6/1994 |
| JP | 7-167865 | 7/1995 |
| JP | 7-287019 | 10/1995 |
| WO | WO 95/00247 | 1/1995 |

*Primary Examiner*—Christopher L. Chin
*Assistant Examiner*—Pensee Do
(74) *Attorney, Agent, or Firm*—McDermott, Will & Emery

(57) ABSTRACT

Technological preposition of the present invention is a liquid processing method making use of a pipette device which sucks a liquid containing a target high molecular substance from inside of a vessel through a chip detachably set on a sucking port or a discharging port of a liquid sucking/discharging line and transfers this liquid or target high molecular substance to the next target processing position for the purpose to execute such works as quantifying, separating, taking out, pipetting, clarifying condensing, and diluting a liquid or a target high molecular substance contained in a liquid and also such works as extracting, recovering, and isolating the target high molecular substance by means of sucking and discharging a liquid with a pipette device and controls by a magnetic body over magnetic particles and/or a filter combined according to the necessity, and the chip can isolate the target high molecular substance by having the substance attracted onto magnetic particles or with a filter set on each chip.

27 Claims, 17 Drawing Sheets

U.S. PATENT DOCUMENTS

| | | | |
|---|---|---|---|
| 5,075,079 A | | 12/1991 | Kerr et al. |
| 5,108,703 A | * | 4/1992 | Pfost et al. ................... 422/65 |
| 5,147,529 A | | 9/1992 | Lee et al. |
| 5,171,537 A | * | 12/1992 | Wainwright et al. ........ 422/100 |
| 5,173,265 A | | 12/1992 | Golias et al. |
| 5,183,638 A | * | 2/1993 | Wakatake .................... 422/64 |
| 5,200,084 A | * | 4/1993 | Liberti et al. ............... 210/695 |
| 5,395,688 A | * | 3/1995 | Wang et al. ................ 428/327 |
| 5,556,598 A | * | 9/1996 | Raybuck et al. .............. 422/10 |
| 5,647,994 A | * | 7/1997 | Tuunanen et al. .......... 210/695 |
| 5,895,631 A | * | 4/1999 | Tajima ....................... 422/101 |
| 5,919,706 A | * | 7/1999 | Tajima ........................ 436/54 |
| 5,976,369 A | * | 11/1999 | Howe et al. ................. 210/222 |
| 6,096,554 A | * | 8/2000 | Tajima ........................ 436/49 |
| 6,100,079 A | * | 8/2000 | Tajima ....................... 435/239 |
| 6,100,094 A | * | 8/2000 | Tajima ........................ 436/54 |

* cited by examiner

LIQUID PROCESSING METHOD MAKING USE OF PIPETTE DEVICE AND APPARATUS FOR SAME

This application is a continuation of U.S. patent application Ser. No. 08/737,946 now U.S. Pat. No. 5,895,631 filed Nov. 20, 1996, and Japanese patent applications No. 8-089050 filed on Mar. 19, 1996 and 7-086005 filed on Mar. 20, 1995.

TECHNICAL FIELD

The present invention relates to a liquid processing method making use of a pipette device and an apparatus for the same, with which works including for quantifying, separating, taking out, pipetting, clarifying, condensing, diluting a liquid or a target high molecular substances included in a liquid such as useful substances such as antibiotic substance, genetic substances such as DNA, and immunological substances such as antibodies, and/or works for extracting, recovering and isolating the target high molecular substance can automatically and accurately be executed by means of absorbing and discharging the liquid through a liquid absorbing/discharging line in the pipette device.

BACKGROUND ART

In recent years, research activities for DNA or the like are very active in many fields including engineering, medical science, agriculture, physical science, pharmacology, and the purpose includes genome sequencing, clinical diagnosis, improvement of agricultural products, bacteriological inspection of foods, drug preparing systems or the like.

As described above, when various types of immunoassay applicable in a very wide range with high expected possibility in its application or structural analysis of molecular level organisms, microorganisms, or substances such as cells, DNA, RNA, mRNA, plasmid, virus, or bacteria (described simply as a target high molecular substance in the present specification) is performed, it is necessary to carry out with high precision works such as those for quantifying, separating, taking out, pipetting, clarifying, condensing, diluting a sample or a target high molecular substance included in the sample or works for extracting, recovering, or isolating a target high-molecular substance as a preprocessing.

To explain structural analysis of a gene such as DNA diagnosis as an example, at first it is necessary to extract, recover, and isolate a DNA region including a target gene. The technology for extracting, recovering, and isolating genes has already been established as the gene cloning technology or genome sequencing technology, and at present it is believed that, by spending enough time and expenses, any gene can be separated and obtained. For this reason, if a target gene DNA has been extracted, recovered, and separated, any type of gene analysis is possible as a principle by making use of the separated gene DNA.

However, in a case of man, for instance, a particular target gene DNA is one millionth or below of all genome DNA, and for this reason actually a quantity of DNA obtainable for testing is quite small, while a quantity of DNA and RNA not necessary for a particular experiment is quite large, which makes it difficult to execute analysis smoothly.

For the reasons as described above, to execute structural analysis of a gene such as DNA diagnosis, it is important to extract, recover, and isolate a DNA area including a target gene. Description is made hereinafter for a basic method of extracting, recovering, and isolating a DNA.

A DNA exist in a nucleus as a complex with a protein in a cell. In the basic sequence for extracting a DNA, a cell or a cell nucleus is processed with SDS (surfactant dodecil sodium sulfate) to make the DNA soluble, and proteins contained therein are removed with a proteolytic enzyme or phenol.

In other words, when a DNA is separated from the tissue, at first the tissue taken out is put in ice and kept therein for a certain period of time under a low temperature, then this cooled tissue is divided to small pieces each with the weight of around 0.1 g, which are washed with a ice-cooled buffer solution A (0.01 M Tris HCl, pH 7.8, 0.1 M NaCl, 2 mM $MgCl_2$). This tissue is put in the above-described buffer solution A having a volume 20 times larger as compared to that of the tissue and is homogenized 5 or 10 times with a Potter type homogenizer. Then the tissue is put in a centrifugal tube together with the buffer solution and is subjected to centrifugation (2,000 rpm, for 5 minutes). The cell nucleus or the cell precipitates, so that the supernatant is aborted. When extracting a DNA from cultured cells, the cells are well suspended in an ice-cooled buffer solution B (0.01 M Tris HCl, pH 7.8, 0.1 M NaCl, 2 mM EDTA) and is subjected to centrifugation. The precipitated nuclei or cells are again well suspended in the buffer solution B having a volume 100 times larger than that of the specimen.

After the cells or cell nuclei are well suspended until a block of cells disappears, a 10% SDS solution is added by one twentieth thereof to lyse the cells. Then proteinase K (10 mg/ml) is added by one fiftieth thereof to the solution and reacted for 4 hours under a temperature of 50° C. so that the protein is lysed. During this reaction, the solution is sometimes agitated because the viscosity is high. Then phenol extraction is executed 3 times. In this step, the extracting work should be performed carefully so that no physical power is not loaded thereto.

Then the specimen is dialyzed for around 18 hours with a buffer solution C (10 mM Tris HCl, pH 7.8/0.1 mM EDTA) having a volume 100 times larger as compared to that of the specimen, and is kept under a temperature of 4° C.

Through the steps as described above, about 0.2 mg of DNA can be obtained from 0.1 g of tissue. What is described above is a process of extracting DNA from tissue or cells, and in addition there have been known a method in which plasmid DNA is obtained by way of the alkali method (the small quantity adjusting method), a method of recovering DNA by way of the boiling method, and a method of recovering closed-cycle bromide DNA by way of the large quantity adjusting method.

As described above, it is possible to extract, recover, and isolate DNA for structural analysis of a gene in, for instance, DNA diagnosis according to any of the known methods as described above, but a work for isolating DNA from the tissue or cells as described above is, as clearly understood from the sequence for extracting DNA from the tissue or cells as described above, extremely complicated, and a long period of time is required, which is disadvantageous.

In addition, any of various types of method including the centrifuging method, high speed liquid chromatography method, gel electrophoresis method, dispo-column method, dialysis method, glass powder method, magnetic particle cleaning nozzle method has been employed for structural analysis of DNA or the like extracted by the above-described means, and each of the methods has respective advantages and disadvantages, and at present a high precision and stable method for structural analysis has not been developed yet.

Namely, in a case of centrifugation, automation of processes for loading and taking out vessels is very difficult, and also it is very difficult to mechanically separate supernatant from precipitates after centrifugation, and for this reason its applicability for various purpose is disadvantageously poor.

In a case of high speed liquid chromatography, a separation column is basically consumable, injection for a sample to the column or time management for separation can not be mechanized, and also different samples pass through the column, which disadvantageously makes it impossible to completely prevent contamination of the column.

Furthermore, in a case of gel electrophoresis, adjustment of gel can not be mechanized, and this method has generally been used as a basic technique for separation of DNA, but the separated pieces must be taken out manually, which is disadvantageous.

The dispo-column method is one of technic which can be embodied as a kit for separation of a particular DNA piece, but the cost is very expensive, and its applicability is narrow. In addition, controls over pipetting and liquid passing through the column are difficult, and there are many problems in mechanization of this method.

In the dialysis method, a long period of time is required for dialysis, and also it is hard to apply this method when a quantity of sample is small, so that this method has not been used widely.

The glass powder method is an excellent method of extracting DNA making use of silicon dioxide, and the process is simple and convenient, but as the powder is separated with a filter or by way of centrifugation, it is difficult to automate the entire process.

Furthermore in a case of the magnetic particle cleaning nozzle method, the process can be automated by controlling the cylinder and attracting/discharging with magnetic particles, but basically it is impossible to prevent contamination only by cleaning the nozzle.

The present invention was made under the circumstances as described above, and its object is to provide a liquid processing method as well as an apparatus for the same making use of a completely novel pipette device which can automatically and with high precision execute works of quantifying, separating, taking out, pipetting, clarifying, condensing, diluting a liquid or a target high molecular substance contained in a liquid as well as works of extracting, recovering, and isolating the substance by controlling the pipette device's operations for sucking or discharging a liquid and magnetic particles with a magnetic body and/or by a combination of a magnetic body and a filter.

DISCLOSURE OF INVENTION

Technological basis of the present invention is a liquid processing method making use of a pipette device which sucks a liquid containing a target high molecular substance via a chip detachably set in a sucking port or a discharging port of a liquid sucking/discharging line from inside of a vessel and transfers the liquid or the target high molecular substance to a target next processing position, and the chip has the sucked target high molecular substance deposited on magnetic particles and/or separated with a filter set in the chip. Namely, it is possible to automatically execute with high precision the works of quantifying, separating, taking out, pipetting, clarifying, condensing, diluting a liquid or a target high molecular substance as well as works of extracting, recovering, and isolating the substance by controlling the pipette device's operations for sucking and discharging the liquid and magnetic particles with a magnetic body and/or by a combination of a magnetic body and a filter.

Also in the present invention, the target high molecular substance is a useful substance such as antibiotics, genetic substances such ad DNA, or an immunological substance such as antibody. For this reason, the present invention is well suited to works of separating, taking out, pipetting, clarifying, condensing, diluting and/or works of capturing, extracting, isolating, amplifying, labelling, and measuring molecule level organisms or microorganisms such as cells, DNA, RNA, mRNA, plasmid, virus, and bacteria or certain high molecular substance, and a target high molecular substance can be obtained without depending on the conventional centrifugation.

Also in the present invention, such works as quantifying, separating, taking out, pipetting, cleaning, condensing, and diluting the target high molecular substance as described above is carried out with a chip set in the liquid sucking/discharging line described above and at least one type of filter set in a tip section of the chip. With this configuration, such works as quantifying, separating, taking out, pipetting, clarifying, condensing, and diluting the target high molecular substance can easily be executed with high precision.

The present invention is embodied mainly as described above, but by providing a plurality of filter holders in multiple stages in a way where, for instance, a filter holder with a filter to screen out blood corpuscle shells is provided in the first stage of the chip and a filter holder with a silica membrane filter to capture DNA is provided in the second stage thereof, such works as quantifying, separating, taking out, pipetting, clarifying, condensing, and diluting the target high molecular substance as described above can more easily be carried out with high precision. It is needless to say that, in a case where separation of a target high molecular substance is executed by setting each filter holder according to the present invention, the chips and filter holders may be engaged in and processed one by one or complied in a multiple stages and set to execute a plurality of works simultaneously.

Also in the present invention, by using a plurality of filters each having a different pore size (transmission diameter of each filter) and used for separation of a target high molecular substance and foreign materials other than the target high molecular substance respectively, it is possible to obtain only the target high molecular substance without fail.

Also in the present invention, after such works as quantifying, separating, taking out, pipetting, clarifying, condensing, diluting a liquid or a target high molecular substance with the filter as described above, in a step of detachably setting a new chip in a tip section of the liquid sucking/discharging line and sucking/discharging a solution containing magnetic particles with this chip, as the magnetic particles are attracted by a magnetic body provided in the side of the chip onto an internal surface of the chip to extract, recover, and isolate the target high molecular substance, such works as quantifying, separating, taking out, pipetting, clarifying, condensing, and diluting and also such works as extracting, recovering, and isolating a target high molecular substance can automatically be executed.

Also in the present invention, different from a liquid processing based on the filter system as described above, such works as capturing, extracting, isolating, amplifying, labelling, and measuring the target high molecular substance may be executed only with a chip set in the liquid sucking/discharging line, a magnetic force, and one or a plurality types of magnetic particles and without using the filter as described above, more precise liquid processing can be realized with simpler configuration.

Also in the present invention, by causing the chip set in the liquid sucking/discharging line as described above to react with magnetic particles like in the invention described above, refining process such as capturing cells, having cell cores or protein lysed can automatically be executed, and a particular target high molecular substance can easily be extracted, recovered, and isolated.

Furthermore in the present invention, by using magnetic particles with a probe or biotin or streptoavidin coated thereon by making use of a chip set in a liquid sucking/discharging line like in the invention described above after the work of extracting the substance, a particular base sequence piece can easily be isolated with high precision without executing centrifugation.

Also in the present invention, it is possible to execute a series of works for refining such as capturing cells, or having cell core or protein lysed by causing a chip set in the liquid sucking/discharging line to react with magnetic particles for extracting a particular high molecular substance and then isolating the particular base sequence piece with other type of magnetic particles with a probe or biotin or streptoavidin coated thereon easily in a liquid sucking/discharging line in a pipette device.

Also in the present invention, after a series of works such as capturing, extracting, and isolating a target high molecular substance by using the magnetic particles as described above, by making the isolated particular base sequence piece emit light through chemical luminescence or fluorescence or enzymatic coloration, presence or a quantity of the particular base sequence piece can easily be detected or measured.

Also in the present invention, it is possible to easily and automatically execute a series of works for refining such as capturing cells, or having cell core or protein lysed by causing a chip set in the liquid sucking/discharging line to react with magnetic particles for extracting a particular high molecular substance, then amplifying the extracted target high molecular substance, isolating the particular base sequence piece with other type of magnetic particles with a probe or biotin or streptoavidin coated thereon and then detecting presence of or measuring a quantity of the particular base sequence piece by causing the isolated piece to emit light through chemical luminescence or fluorescence or enzymatic coloration.

In the present invention, by executing the works of separating, taking out, pipetting, clarifying, condensing, diluting the target high molecular substance and/or works for capturing, extracting, isolating, amplifying, labelling, and measuring the substance in a single liquid sucking/discharging line or a plurality of liquid sucking/discharging lines provided in parallel to each other, a sequences of works can be executed efficiently and automatically. In a case where a plurality of liquid sucking/discharging lines are provided in parallel, the processing capacity is improved, and also a multi-channel processing line can be realized.

In the present invention, in a case where processing is executed with a plurality of liquid sucking/discharging lines provided in parallel, as the plurality of liquid sucking/discharging lines are driven and controlled so that the works of separating, taking out, pipetting, clarifying, condensing, diluting the target high molecular substance and/or the works of capturing, extracting, isolating, amplifying, labelling, and measuring the substance in each line are executed according to the same timing, or also so that each liquid is sucked or discharged in a specified processing step according to a different timing, and for this reason processing steps suited to a target high molecular substance can easily be built up.

In the present invention, by providing working spaces separated from each other with partitions in the single or a plurality of liquid sucking/discharging lines, or by providing working spaces with an air flow by means of continuously sucking air in each line working space from an air sucking port, or by combining these different types of configuration, even in a case of liquid processing such as extracting and analyzing DNA or the like in which it is required to strictly prevent contamination by air in each processing line, the objective can easily be achieved.

Also in the present invention, by having a target high molecular substance or a substance bonded to a target high molecular substance absorbed or bonded to a surface of each magnetic particle used for the purpose of the present invention, the target high molecular substance can be obtained without executing centrifugation.

In the present invention, in a case where the above-described magnetic particles are used, controls are provided so that the magnetic particles are absorbed onto an internal wall of a chip due to a magnetic force working from outside of the chip, or so that, if effect of the magnetic force is weak or not present, the magnetic particles are held separable from the internal surface of the chip, it is possible to control capture of target high molecular substance and separation of the same from foreign materials with high precision.

In the present invention, by controlling load of a magnetic force into or elimination of a magnetic force in a chip by means of moving a permanent magnet in a direction perpendicular to the longitudinal direction of the chip or in a range including the direction perpendicular to the longitudinal direction of the chip, or by turning ON or OFF an electric magnet, it is possible to efficiently execute such works as absorbing magnetic particles or agitating and mixing the magnetic particles with other liquid or cleaning.

In the present invention, in a case where processing is executed with an electric magnet, by turning ON the electric magnet when it contacts an external surface of the chip to generate a magnetic force or by moving off the electric magnet from the chip when the magnetic force is eliminated, absorption of magnetic particles or agitation and mixing of magnetic particles with other solution or cleaning can efficiently be executed.

In the present invention, when removing a chip from a liquid sucking/discharging line, it can easily be removed by holding the chip with a holding body synchronously operating when the permanent magnet or electric magnet moves to the chip and the permanent magnet or electric magnet and then moving the liquid sucking/discharging line upward.

In the present invention, the chip described above comprises a small diameter section steeped into a liquid, a large diameter section having a capacity larger than a capacity of a vessel in which a liquid is accommodated, and an intermediate section provided between the small diameter section and the large diameter section and having a diameter smaller at least than that of the large diameter section, and magnetic particles are captured by the intermediate section, so that clogging never occurs and the magnetic particles can almost completely be absorbed because of magnetism within a short period of time.

In the present invention, an internal diameter of the intermediate section of a chip described above has a dimension appropriate for ferromagnetic field of the magnetic body to provide effects therein, and magnetic particles are captured due to a magnetic force generated in the ferromagnetic field of the magnetic body, so that magnetic particles can almost completely be captured because of magnetism within a short period of time.

In the present invention, by forming an internal diameter of the intermediate section of a chip described above so that it has the substantially same width dimension as that of a contacting surface of a magnetic body contacting the intermediate section, the most effective absorption of magnetic particles can be realized.

In the present invention, absorption of magnetic particles onto an internal surface of a chip set in the liquid sucking/discharging line is executed by passing a solution containing magnetic particles through a ferromagnetic field inside a chip at a slow speed appropriate for the magnetic particles to be captured completely, the magnetic particles can completely be captured.

In the present invention, controls are provided so that the final liquid surface of a liquid passing through the chip when sucked into or discharged from the chip always reaches the magnetic field described above, so that the magnetic particles can be captured more completely.

In the present invention, in a case where a liquid is sucked or discharged with a so-called single nozzle, the liquid is sucked by contacting a tip section for a chip set in the liquid sucking/discharging line to an internal bottom of a vessel with the liquid accommodated therein and then lightly raising the tip section, so that almost all of the liquid within the vessel can be sucked and uniformity of reaction can be maintained.

In the present invention, agitation and mixing of magnetic particles absorbed in the chip with a reagent or cleaning water is executed under the so-called pumping control in which the works of sucking and discharging the liquid in the liquid sucking/discharging line is continuously executed at a high speed and times enough to agitate and mix the liquid with the magnetic particles, so that the liquid and magnetic particles can homogeneously be agitated and mixed with each other.

In the present invention, in a case where the works of agitating and mixing a liquid and magnetic particles with each other are executed, the works of sucking and discharging the liquid in the liquid sucking/discharging line is executed with the tip section steeped into a reagent or cleaning water accommodated in a vessel so that a quantity of a liquid in the vessel and a sucking/discharging rate substantially coincide with each other, and for this reason no bubble is generated and the reaction can be executed under no physical impact, so that separation of a target high molecular substance from the magnetic particles due to bubbles can be prevented without fail.

In the present invention, in a case where necessary temperature controls are provided to promote a reaction between a target high molecular substance and a reagent or the like or amplification of the target high molecular substance, the reaction liquid or a liquid to be amplified is transferred with the chip into each thermostatic chamber previously kept in a specified temperature to be heated or cooled therein, so that a period of time required for heating or cooling the reaction liquid or the liquid to be amplified can substantially be reduced.

In the present invention, when controlling a temperature in each reaction chamber, a covering body is set over a tip section of the liquid sucking/discharging line, and the covering body is set via the liquid sucking/discharging line on the thermostatic chamber, so that evaporation of the liquid can be prevented and also contamination of air can be prevented without fail.

In the present invention, the covering body is built so that it is plucked and broken by the liquid sucking/discharging line or a chip set in the line, and for this reason it is not necessary to provide a separate sucking/discharging means, and a reaction liquid or a liquid to be amplified in a thermostatic vessel can be sucked by the liquid sucking/discharging line or a chip set therein, so that the configuration is quite simple and a series of works can automatically be executed.

In the present invention, to realize each of the liquid processing methods as described above, there is provided a liquid processing apparatus making use of a pipette device comprising a liquid sucking/discharging line which can move in the horizontal direction and is maintained at a specified position so that it can move in the vertical direction, a means for executing liquid sucking/discharging works through the liquid sucking/discharging line, a plurality of chips required for processing one type of liquid and provided along the horizontal direction in which the liquid sucking/discharging line moves, a vessel with the liquid accommodated therein, one or more filter holders each having a filter required for the processing above, and one or more vessels each having other type of liquid required for the processing above, and the liquid sucking/discharging line or a chip set therein is driven and controlled according to instructions from a control unit so that the chip is transferred with a filter holder set therein to execute such works as quantifying, separating, taking out, pipetting, clarifying, condensing, and diluting the liquid or a target high molecular substance contained in the liquid, and for this reason it is not necessary to especially provide a means in which an operation may be interrupted such as a centrifugal separator, and it is possible to automate such works as quantifying, separating, taking out, pipetting, clarifying, condensing, diluting a target high molecular substance with simple configuration.

In the present invention, there is provided a liquid processing apparatus comprising a liquid sucking/discharging line which can move in the horizontal direction and is maintained at a specified position so that it can move in the vertical direction, a means for executing liquid sucking/discharging works through the liquid sucking/discharging line, a plurality of chips required for processing one type of liquid and provided along the horizontal direction in which the liquid sucking/discharging line moves, a vessel with the liquid accommodated therein, a magnetic body for attracting magnetic particles contained in a liquid onto an internal surface of a chip when the liquid is sucked into or discharged from the chip, one or more vessels with other types of liquid accommodated therein respectively required for the processing described above, and the liquid sucking/discharging line or the chip is driven and controlled according to instructions from a control unit so that the chip is transferred to execute such works as capturing, extracting, isolating, amplifying, labelling, and measuring a liquid or a target high molecular substance contained in the liquid, and for this reason it is not necessary to especially provide a means in which the operation such as a centrifugal separator may be interrupted, and also it is possible to automate such works as capturing, extracting, isolating, amplifying, labelling, and measuring a target high molecular substance with simple configuration.

In the present invention, there is provided a liquid processing apparatus making use of a pipette device comprising a liquid sucking/discharging line which can move in the horizontal line and is maintained at a specified position so that it can move in the vertical direction, a plurality of chips required for processing one type of liquid and provided along the horizontal line in which this sucking/discharging line moves, a vessel with the liquid accommodated therein, one or more filter holders each having a filter set therein required for the processing described above, one or more vessels each accommodating therein other types of liquid required for the processing above, a vessel in which a liquid containing magnetic particles is accommodated, and a magnetic body for attracting the magnetic particles onto an internal surface of the chip in the process of sucking or discharging a solution containing the magnetic particles, and the liquid sucking/discharging line is transferred according to instructions from a control unit to execute required processing for a liquid or a target high molecular substance contained in the liquid, and for this reason it is possible to execute such works as quantifying, separating, taking out, pipetting, clarifying, condensing, diluting a target high molecular substance and also such complicated works as extracting, recovering, and isolating the target high molecular substance with very simple configuration in succession and automatically.

In the present invention, a hook for locking and supporting a chip engaged in and supported by the liquid sucking/discharging line is rotatably supported by the liquid sucking/discharging line, and the hook is energized in its normal state in the direction in which connection between the liquid sucking/discharging line and the chip is maintained, and also the hook is energized by a lock releasing body provided at a specified position in the direction in which locking between the liquid sucking/discharging line and the chip is released, so that it is possible, when a filter holder is set in or removed from a tip section of a chip, to prevent the chip from being separated from the liquid sucking/discharging line without fail, and also locking with the hook can automatically be released.

In the present invention, in a case of a liquid processing apparatus with the hook attached thereto, the filter holder set in a tip section of the chip is transferred so that the chip and/or the filter holder is separated from an edge of the liquid sucking/discharging line or a chip set therein when the liquid sucking/discharging line locked by the locking body is moved upward, so that the work of removing a chip and/or a filter holder can be automated.

In the present invention, the vessel used according to the present invention is formed into a cassette form having a plurality of chambers each for accommodating a type of liquid therein and then samples or reagents required for a reaction or processing can be pipetted to each of the liquid accommodating section, so that high precision liquid processing can be realized. In this case, a portion or all of the reagent previously accommodated in each liquid accommodating section is shielded with a thin film body which can be broken by the liquid sucking/discharging line or a chip set thereon, and a mechanism for pipetting each reagent becomes unnecessary, which is desirable for simplifying configuration of an apparatus.

In the present invention, in a case where the magnetic body is built with a permanent magnet, a surface of the permanent magnet contacting a chip is formed according to an external form of the chip and the chip is movably provided in a direction perpendicular to the longitudinal direction of the chip, so that it is possible not only to completely capture magnetic particles, but also to prevent adverse effects by diffusion and movement of the magnetic particles in association with the magnet without fail.

In the invention, the magnetic body is built with an electric magnet in place of the permanent magnet described above with a surface thereof contacting a chip formed according to an external form of the chip, and is provided so that the electric magnet generates a magnetic force when it contacts outside of the chip and also can move, when degaussed, in a direction perpendicular to the longitudinal center line of the chip or in a range including the direction, and for this reason magnetic particles are attracted in association with movement of the magnetic body along the longitudinal center line of the chip so that it is possible to prevent the magnetic particles from going out of control and control over the magnetic particles from being lost, which makes it possible to realize complete attraction of the magnetic particles.

In the present invention, a holding body, which moves, when the permanent magnet or electric magnet moves to the chip, in synchronism to movement of the magnet, is provided, a surface of the holding body contacting a chip is formed according to an external form of the chip, and the chip is held between the holding body and the permanent magnet or electric magnet, so that the chip can easily be removed only by moving the liquid sucking/discharging line upward.

In the present invention, a temperature control step required for a reaction between a target high molecular substance and a reagent or the like or for amplifying the target high molecular substance is inserted into the liquid processing step with the liquid sucking/discharging line, the reaction liquid or the liquid to be amplified is transferred with the chip to each thermostatic vessel kept at a prespecified temperature, and also a covering body, which can be set in a tip section of the liquid sucking/discharging line, is set by the liquid sucking/discharging line on each thermostatic vessel in which the reaction liquid or the liquid to be amplified is accommodated, so that also amplification of the target high molecular substance can successively be processed in a series of works.

Furthermore in the present invention, the covering body comprises a flat surface section having a diameter larger than that of a bore of the thermostatic vessel and a maintenance groove section formed in a substantially central portion of the flat surface section and having the same bore as an external diameter of the liquid sucking/discharging line or the tip of the chip, and a bottom section of the maintenance groove section is formed with a thin film body which can be broken by the liquid sucking/discharging line or the chip, so that it is not necessary to separately provide a covering body supply means or a liquid sucking/discharging means, which largely simplifies this type of apparatus.

BRIEF DESCRIPTION OF DRAWINGS

FIG. 17A is an enlarged view of a portion of FIG. 17.

BEST MODE FOR CARRYING OUT INVENTION

Detailed description is made for the present invention with reference to embodiments thereof shown in the related drawings.

Figure 1:
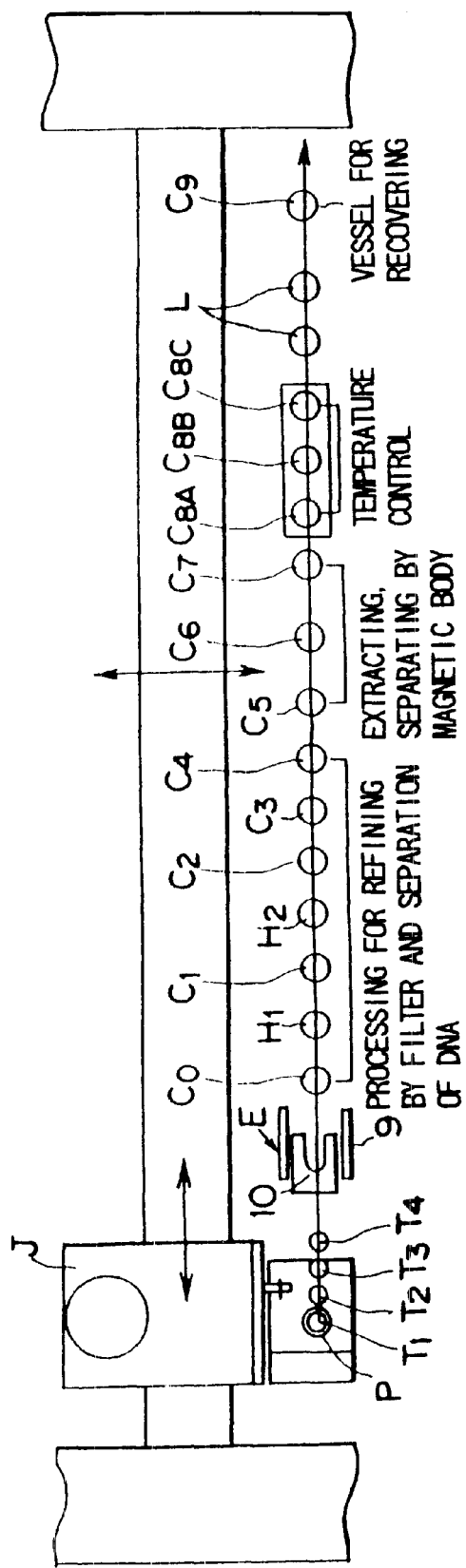
FIG. 1 is a flat explanatory view showing general configuration of an apparatus for extracting, recovering, and isolating DNA according to the first embodiment of the present invention.

FIG. 1 shows an example of configuration in which the present invention is applied to an apparatus for extracting, recovering, and isolating DNA.

This apparatus comprises a pipette nozzle P supported by a nozzle unit so that it can freely be moved by an XYZ moving mechanism in the vertical direction as well as in the horizontal direction, chips $T_1$, $T_2$, $T_3$, and $T_4$ arranged from left to right in the FIG. 1, a chip removing body E, a sample vessel $C_0$, a first filter holder $H_1$, a cell $C_1$, a cell $C_2$, a cell $C_3$, a second filter holder $H_2$, a cell $C_4$, a cell $C_5$, a cell $C_6$, a cell $C_7$, a thermostatic cell $C_{8A}$, a cell $C_{8B}$, a cell $C_{8C}$, and a DNA recovery cell $C_9$.

Namely in this embodiment, the chips $T_1$, $T_2$, $T_3$ have a form suited for holding the filter holders $H_1$, $H_2$, and the chip $T_4$ has a form suited for capturing magnetic particles. It should be noted that, although the description of the embodiment above assumes a case where a chip for capturing magnetic particles is processed with only one chip $T_4$, the form is not limited to that described above, and that a plurality of chips may be used according to the needs in the processing step.

Also it should be noted that also in this embodiment, up to the first filter holder $H_1$, cell $C_1$, second filter holder $H_2$, cell $C_2$, cell $C_3$, cell $C_4$ controls the step of refining with a filter.

Also the cell $C_5$, cell $C_6$, and cell $C_7$ controls the magnetic reaction as well as the steps of extracting and isolating, and furthermore the thermostatic cell $C_{8A}$, cell $C_{8B}$, and cell $C_{8C}$ control temperature in the reaction.

As described above, by arranging the cells sequentially, processing can be executed in a state where a plurality of specimens of a sample are arranged in an array, and also control for driving the pipette nozzle P can be simplified. It is needless to say that arrangement of the cells may be combined or changed according to the processing sequence.

It is desirable that the pipette nozzle P is connected directly or with a certain but small range to a cylinder which can strictly control a sucking/discharging rate with a servo motor or a pulse motor and unitized therewith.

Figure 2:
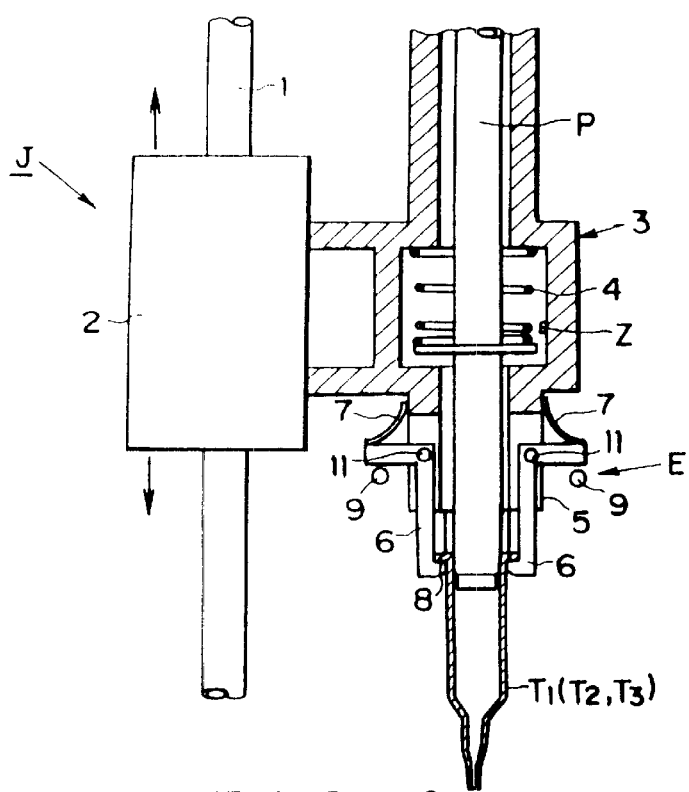
FIG. 2 is a cross-sectional view showing general configuration of a nozzle unit in the apparatus.

A nozzle unit J supporting this pipette nozzle P comprises, as shown in FIG. 2, a vertical movement guide body 1 movably supported in the XY direction (horizontal direction), a holder 2 connected with the vertical movement guide body 1 and moving in the vertical direction, a supporting body 3 extending in the horizontal direction from this holder 2, the pipette nozzle P penetrating this supporting body 3 in the vertical direction and supported thereby, a spring 4 provided in the supporting body 3 and energizing the pipette nozzle P in the downward direction in its normal state, and a hook bodies 6, 6 rotatably supported on the opposite side to a lower projecting section 5 of the supporting body 3. It should be noted that the sign Z in the figure indicates a sensor controlling a downward moving rate of the pipette nozzle P.

The hook bodies 6, 6 are energized in its normal state in the closing direction due to an energizing force of the sheet springs 7, 7 fixed to the lower projecting section 5. It should be noted that the spring 4 above is provided as a cushion for the pipette nozzle P, so that it may be provided in any portion of the pipette nozzle P or the supporting body 3, and also the sheet springs 7, 7 may directly be attached to the pipette nozzle P.

The nozzle unit having the configuration as described above is built so that it can move in the XYZ directions (in the horizontal direction and in the vertical direction) with the chips $T_1$, $T_2$, $T_3$ engaged in a tip section of the pipette nozzle P supported by this nozzle unit J, and this engagement is maintained because the hook bodies 6, 6 locks a flange 8 Of the chips $T_1$, $T_2$, and $T_3$ in the state in which the hook body holds and embraces the chips.

Figure 3:
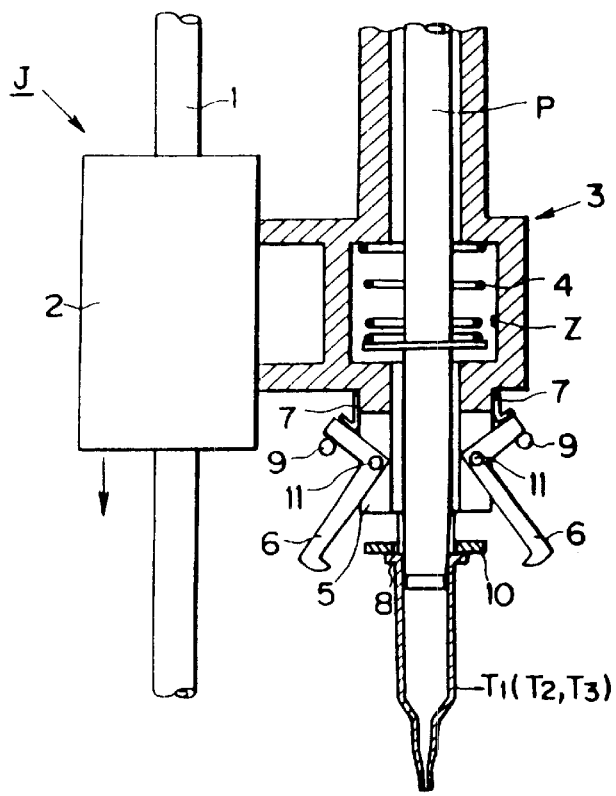
FIG. 3 is an explanatory view explaining a step of removing a chip with a hook body in the nozzle unit.
Figure 4:
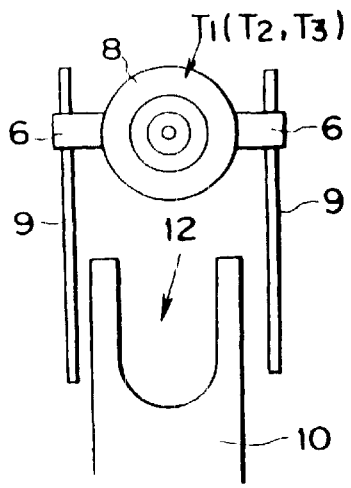
FIG. 4 is a flat explanatory view showing a state before U-shaped body for removing the chip and the chip are engaged with each other.
Figure 5:
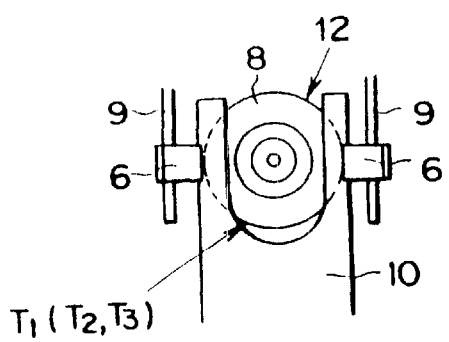
FIG. 5 is a flat explanatory view showing a state after the U-shaped body for removing the chip and the chip are engaged with each other.
Figure 6:
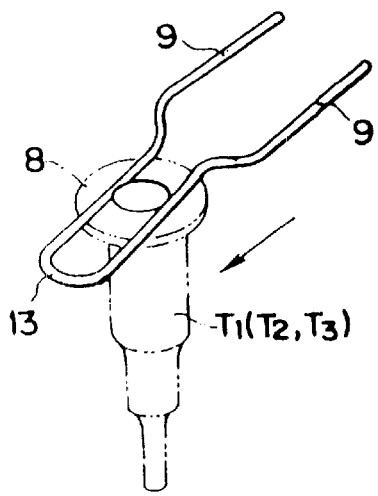
FIG. 6 is a perspective view showing a case where the U-shaped body is formed with a locking release rod.

The chip removing body E for releasing connection (locked state) with the hook bodies 6, 6 between the pipette nozzle P and the chips $T_1$, $T_2$, and $T_3$ comprises a pair of lock releasing rods 9, 9 provided at a position for aborting chips as shown in FIG. 2 and FIG. 3, a U-shaped body 10 having, for instance, a sheet form provided at the bottom of the lock releasing rods 9, 9 as shown in FIG. 4 and FIG. 5, and deposition tank (not shown) into which the chips $T_1$, $T_2$, $T_3$ separated from the pipette nozzle P are aborted.

As described above, the pipette nozzle P and chips $T_1$, $T_2$, $T_3$ are locked and supported by the hook bodies 6, 6 to prepare against a discharging pressure of the liquid, or because the engagement between the pipette nozzle P and the chips $T_1$, $T_2$, $T_3$ should not have been released when separating the filter holders $H_1$, $H_2$. from the chips $T_1$, $T_2$, $T_3$.

For this reason, when releasing connection with the hook bodies 6, 6 between the pipette nozzle P and the chips $T_1$, $T_2$, $T_3$, at first the nozzle unit J is moved downward at a position where the chip removing body E is provided.

Then horizontal flange sections 6a, 6a of the hook bodies 6, 6 contact the rock releasing rods 9, 9, and when the nozzle unit J moves further downward, the hook bodies 6, 6 rotate in the opening direction around shafts 11, 11 as a support as shown in FIG. 3, and the locked state between the pipette nozzle P and the chips $T_1$, $_{T2}$, $T_3$ are released.

From the state described above, the nozzle unit J moves in the horizontal direction, and as shown in FIG. 4, the flange 8 of each of the chips $T_1$, $T_2$, $T_3$ moves to a lower surface of the U-shaped body 10 with a body section of the pipette nozzle P engaged in a U-shaped groove section 12 of the U-shaped body 10, and then, when the nozzle unit J goes upward, the flange 8 of the chips $T_1$, $T_2$, $T_3$ contact a peripheral section of the U-shaped groove section 12 of the U-shaped body 10, the upward movement thereof is restricted, so that only the pipette nozzle P goes upward and the chips $T_1$, $T_2$, $T_3$ are scraped away from the pipette nozzle P.

The description of the U-shaped body 10 above assumes a case where the U-shaped groove section 12 is provided in a plate body, but the same effect can be achieved by connecting edge sections 13 of the lock releasing rods 9, 9 in a U-shaped form and forming them into a monolithic form.

This lock releasing rods 9, 9 and the U-shaped body 10 may be provided not only at a position where the chip removing body E is provided, but also at any of necessary positions described later.

By the way, in this embodiment, the chips $T_1$, $T_2$, $T_3$ are used as a set. It is needless to say that the number of chips may be increased or reduced according to the processing sequence. Also a number of cell $c_6$ and cell $C_7$ is not limited to that in the embodiment shown in the figure, and may be increased or reduced according to the necessity.

Figure 7:
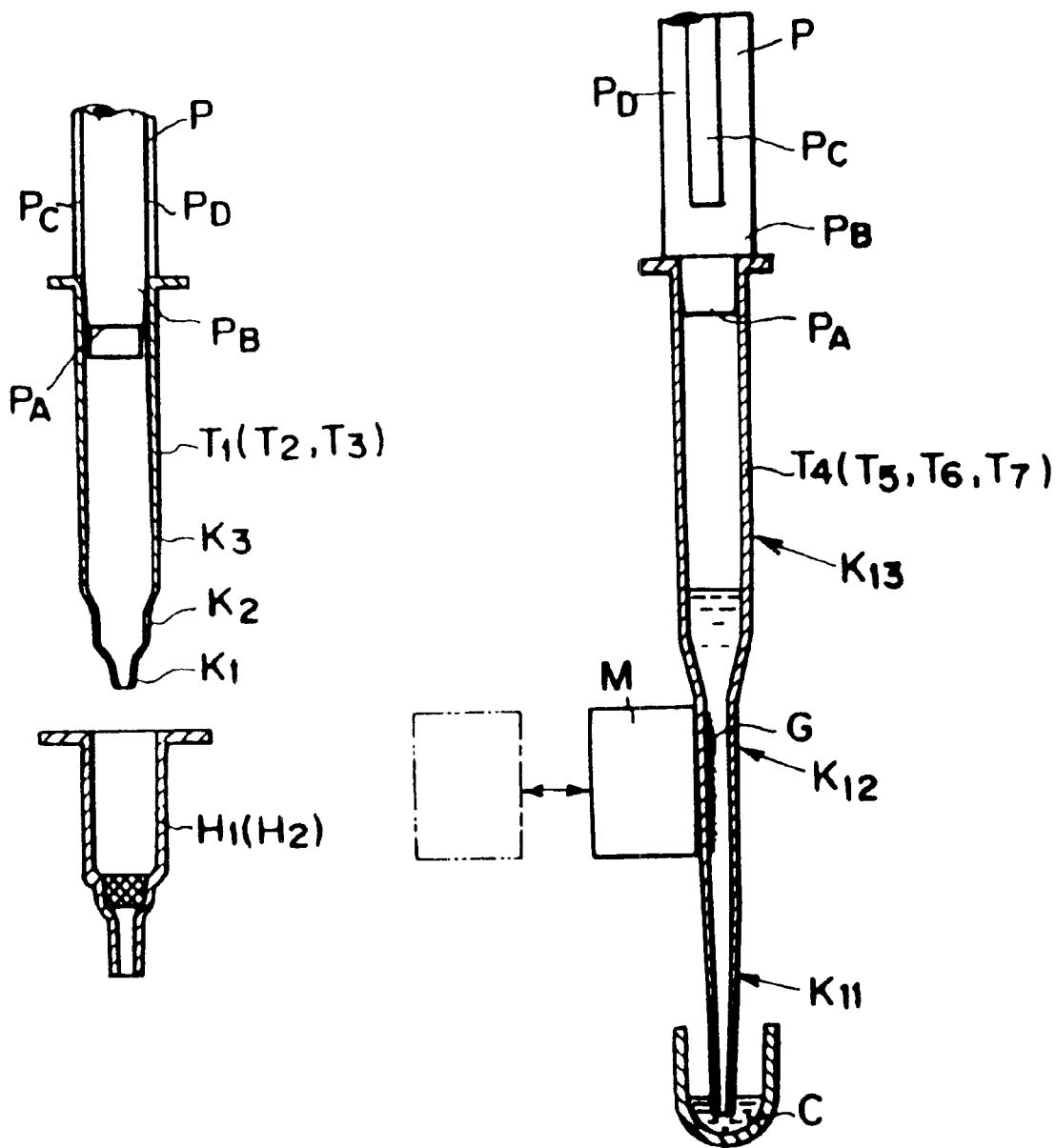
FIG. 7 is a cross-sectional view showing an example of forms of two chips used in the present invention.

And formed in a lower edge section of the pipette nozzle P are 2 stage sections $P_A$, and $P_B$ as shown in FIG. 7, and the chips $T_1$, $T_2$, $T_3$ are detachably set in the first stage section $P_A$, while the chip $T_4$ is detachably set in the second stage section $P_B$.

Figure 8:
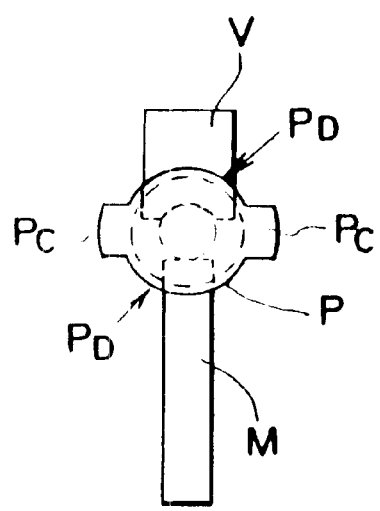
FIG. 8 is an explanatory view showing configuration of a pipette nozzle and a positional relation between a holding body and a magnetic body when getting closing to or away from each other.

Furthermore in the lower edge section of the pipette nozzle P, as shown in FIG. 8, a surface with flanges $P_C$, $P_C$ each projecting outward from the peripheral surface and a surface $P_D$ crossing the flanges $P_C$, $P_C$ are formed into a flat surface respectively.

As described above, by providing the flanges $P_C$, $P_C$ in a projecting form, it is possible to remove the chips $T_1$, $T_2$, $T_3$ with the removing body E, and also by having a surface $P_D$ formed into a flat surface form, it is possible to remove the chip T by holding it between the holding body V and a magnetic body M.

Figure 9:
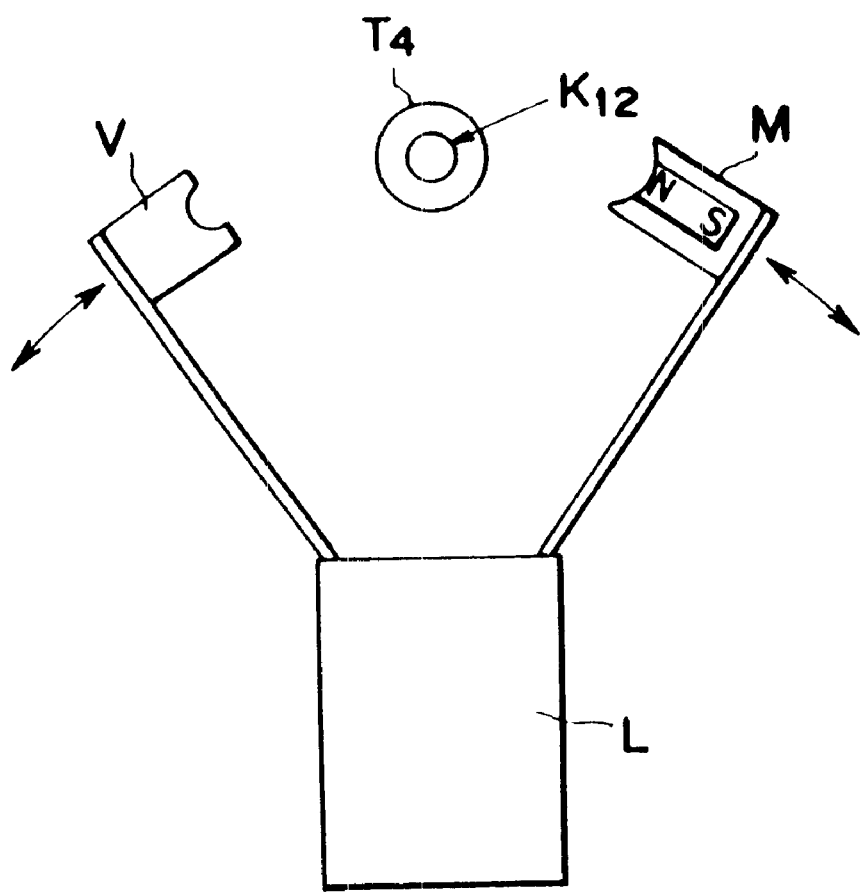
FIG. 9 is a flat explanatory view showing configuration of a magnetic body as well as that of a holding body used in this embodiment.
Figure 10:
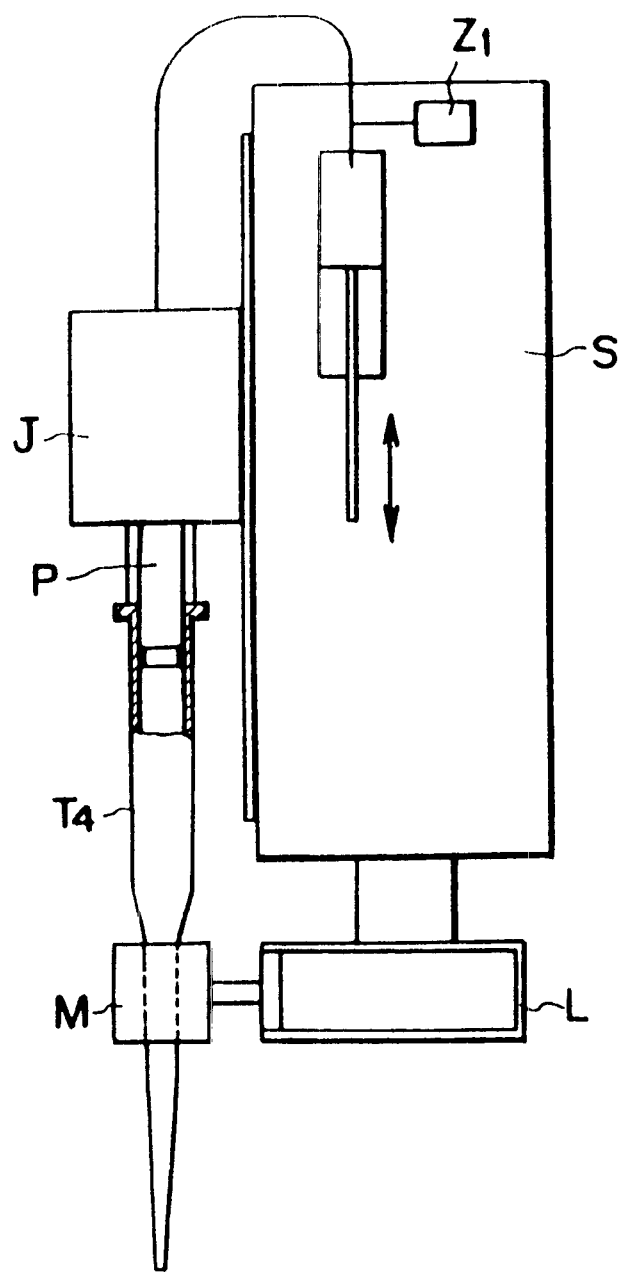
FIG. 10 is an explanatory view showing positions at which the magnetic body and holding body are attached respectively.

In this holding body V and the magnetic body M, a known gear mechanism or a cam mechanism is, as show in FIG. 9, constructed so that it opens or closes in synchronism to an operation of an opening/closing mechanism L comprising a rack and pinion mechanism or the like, and the opening/closing mechanism L is provided in a lower section of the cylinder unit S as shown in FIG. 10.

Also in the holding body V, a surface contacting the chip $T_4$ is formed into a concave form according to an external form of an intermediate diameter section $K_{12}$ of the chip $T_4$, and by holding the chip $T_4$ between the holding body V and the magnetic body M and then moving the pipette nozzle P upward, it is possible to easily remove the chip $T_4$.

Setting of each of the chips $T_1$, $T_2$, $T_3$, and $T_4$ having the configuration as described above is executed, for instance, by transferring the pipette nozzle P to just above a chip rack (not shown) with the chips $T_1$, $T_2$, $T_3$, $T_4$ supported thereon in at an erected position, then descending the pipette nozzle P, and press-fitting the lower edge section $P_A$ or $P_B$ of the pipette nozzle O into upper edge sections of the chips $T_1$, $T_2$, $T_3$, $T_4$.

Namely each of the chips $T_1$, $T_2$, $T_3$ each with the filter holders $H_1$, $H_2$ set thereon comprises, as shown in FIG. 7, a small diameter section $K_1$, an intermediate diameter section $K_2$ connected to an upper section of this small diameter section $K_1$, and a large diameter section $K_3$ connected to an upper section of this intermediate diameter section $K_2$, all of which are connected to each other in the vertical direction and formed into a monolithic form, and the filter holder $H_1$, $H_2$ described later are detachably set in the intermediate diameter section $K_2$.

The intermediate diameter section $K_2$ of each of the chips $T_1$, $T_2$, $T_3$ has the substantially same diameter as or a slightly larger diameter than an inner diameter of the engaging section between the filter holders $H_1$, $H_2$, and length of the small diameter section $K_1$ is short enough for tip sections of the filter holders $H_1$, $H_2$ not to contact a filter when the filter holders $H_1$, $H_2$ are engaged.

On the other hand, the chip $T_4$ to which magnetic particles are attracted is different in the purpose of its use as well as in the method of using it from the chips $T_1$, $T_2$, $T_3$ with filter holders set thereon respectively, and the chip $T_4$ comprises, as shown in FIG. 7, the large diameter section having an internal bore engaged onto the second stage section $P_B$ which is smaller than the first stage section $P_A$ of the pipette nozzle P, the intermediate diameter section $K_{12}$ having a diameter smaller than that of the large diameter section $K_{13}$, and the small diameter section $K_{11}$ having a diameter smaller than that of the intermediate diameter section $K_{12}$, and a magnetic body M attracting magnetic particles is moved to or away from the intermediate section $K_{12}$.

Figure 11:
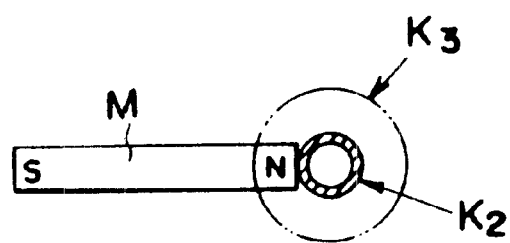
FIG. 11 is a cross-sectional view for explanation of a relation between a bore of an intermediate diameter section of a chip and a width dimension of a magnetic body.

An internal diameter of the intermediate diameter section $K_{12}$ of this chip $T_4$ has a dimension enough for a ferromagnetic field of the magnetic body M to be effective therein, and preferably the dimension is, as shown in FIG. 11, substantially identical to a width dimension of the surface of the chip to which the magnetic body M contacts.

It should be noted that, although the description of the present embodiment above assumes a case where, from each of the chips $T_1$, $T_2$, $T_3$ only the filter holders are removed, but in a case of a reaction step in which only the filter holders $H_1$, $H_2$ are not required to be removed, locking with a hook body is not required, so that a bore of the large diameter section of a chip for a filter holder may be the same as that of the chip $T_4$.

Figure 12:
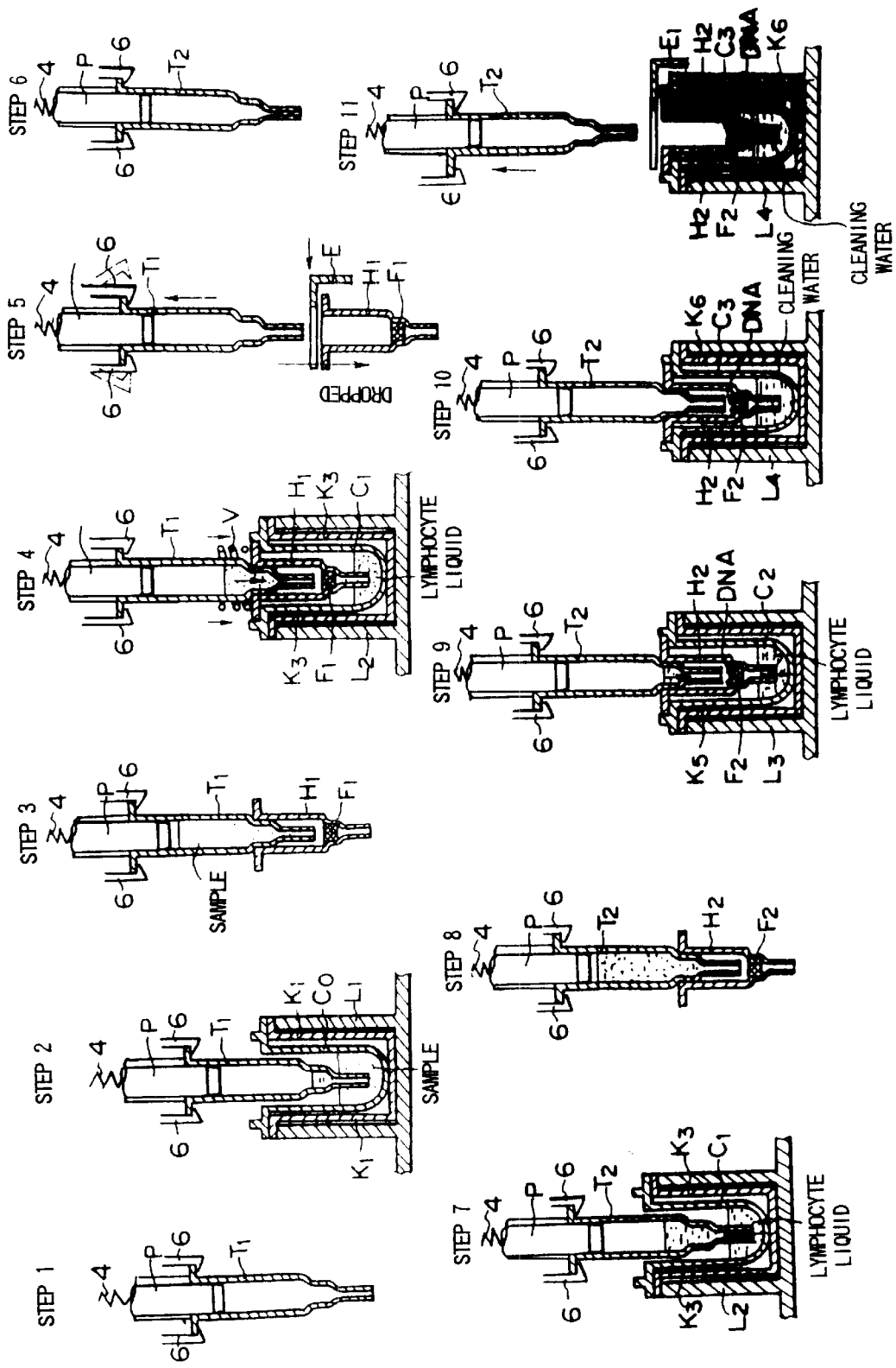
FIG. 12 is a flow chart for explanation of steps from step 1 to step 10 in the works of extracting, recovering, and isolating DNA with the apparatus.
Figure 13:
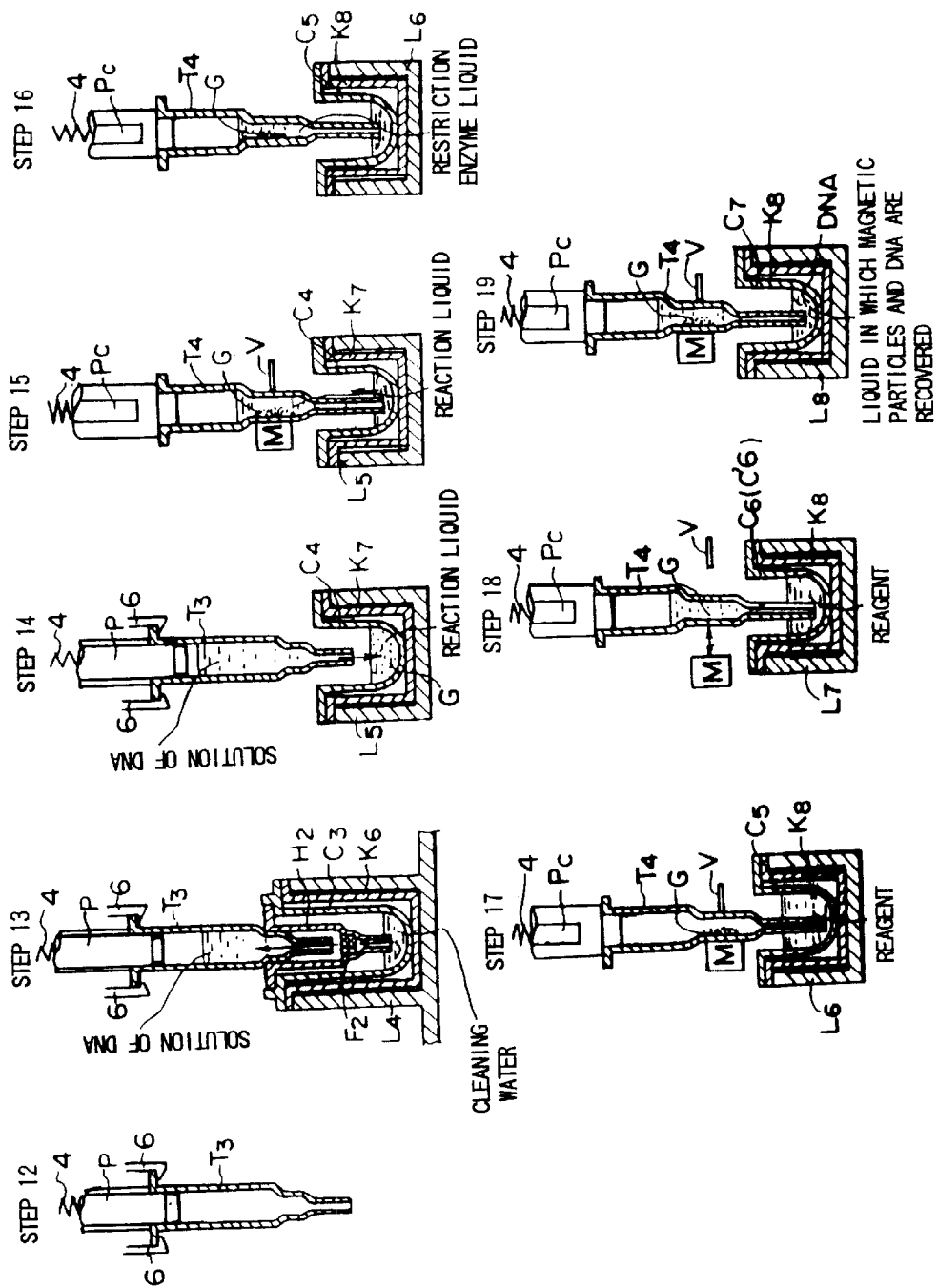
FIG. 13 is a flow chart for explanation of steps from step 12 to step 19 in the works of extracting, recovering, and isolating DNA with the apparatus.

The apparatus for extracting, recovering, and isolating DNA having the configuration as described above is driven and control in the steps shown in FIG. 12 and FIG. 13.

At first, as shown in FIG. 12, in step 1, the first chip $T_1$ is inserted into the first stage $P_A$ in a lower edge section of the pipette nozzle P. In this step, the pipette nozzle P and the chip $T_1$ are locked by the hook bodies 6, 6 and the connection between the two members are maintained.

When the chip $T_1$ has been set in the first stage $P_A$ in the lower edge section of the pipette nozzle P, the pipette nozzle P is transferred to just above the sample vessel $C_0$ with a sample accommodated therein and then goes down with the liquid surface checked by a liquid surface sensor $Z_1$ (Refer to FIG. 10), and then the lower edge section of the chip $T_1$ is inserted into the sample and a required quantity of the sample is sucked (step 2).

The sample used in this embodiment is natural blood having been subjected, before start of experiment, to cell core lysis or protein lysis with such a solution as an SDS solution or a proteinase K solution, but a step of cell core lysis or protein lysis using the above solution may be incorporated in this processing flow.

Then the chip $T_1$ having absorbed a required quantity of sample therein is transferred to just above the first filter holder $H_1$ with the first filter $F_1$ provided therein, and goes down with the first filter holder $H_1$ locked and engaged in a lower edge section of the chip $T_1$ (step 3).

The filter $F_1$ set in this first filter holder $H_1$ can remove blood corpuscle shells in the sample above from the blood dissolved and discharge a lymphocyte solution containing DNA into the cell $C_1$. The pipette nozzle P with the first filter holder $H_1$ locked and engaged in the lower edge section of the chip $T_1$ is then transferred to just above the cell $C_1$, and at the position the pipette nozzle P starts a discharging operation, separates cell membrane and blood corpuscle shells in the sample from lymphocytes and DNA loading reburied pressure to the sample sucked into the chip $T_2$, and discharges only the lymphocytes and DNA into the cell $C_1$ (step 4). At this point of time, as the pipette nozzle P is energized downward by the spring 4, the flange 13 of the first filter holder $H_1$ is pressed and closely adhered to a periphery of an opening of the cell $C_1$, so that generation of leak due to a discharging pressure of the liquid is prevented.

Then the pipette nozzle P is transferred to just above a position where the chip removing body E shown in FIG. 1 is provided, the chip $T_1$ and first filter holder $H_1$ are removed from the lower edge section of the pipette nozzle P according to the processing sequence described above (step 5), and the chip $T_1$ and first filter holder $H_1$ removed as described above are aborted into a waste tank (not shown).

Then the pipette nozzle P is transferred to just above a chip rack with the chip supported in the erected position, and goes down at the position with the second chip $T_2$ set in the first stage $P_A$ in the lower edge section of the pipette nozzle P (step 6). Also in this case, the pipette nozzle P and the chip $T_2$ are locked and connected to each other by the hook bodies 6, 6.

Then the pipette nozzle P with the chip $T_2$ set therein is transferred to just above the cell $C_1$ again and goes down at the position with a required quantity of lymphocyte solution sucked from the cell $C_1$ there (step 7).

Then the pipette nozzle P is transferred to just above the second filter holder $H_2$ with the second silica membrane filter $F_2$ provided therein and goes down there with the second filter holder $H_2$ locked and engaged in a lower edge section of the chip $T_2$ (step 8).

Then the silica membrane filter $F_2$ set in this second filter holder $H_2$ separates DNA from foreign materials in the lymphocyte solution above, and discharges the residual solution into the cell $C_2$.

As described above, the pipette nozzle P with the second filter holder $H_2$ locked and engaged in the lower edge section of the chip $T_2$ is transferred to just above the cell $C_2$, and at the position the pipette nozzle P starts an discharging operation, separates DNA from foreign materials in the lymphocyte solution loading required pressure to the lymphocyte solution sucked into the chip $T_2$, and discharges the residual lymphocyte solution into the cell $C_2$ (step 9). In this step, as the pipette nozzle P is energized downward by the spring 4, the flange 14 of the second filter holder $H_2$ is pressed and closely adhered to a periphery of an opening of the cell $C_2$, so that generation of leak due to a discharging pressure of the liquid is prevented.

Then the pipette nozzle P with the second filter holder $H_2$ having captured DNA and locked and engaged therein is transferred to just above the third cell $C_3$ in which a cleaning liquid is accommodated, and goes down there with the second filter holder $H_2$ steeped into the cleaning liquid in the cell $C_3$ (step 10).

Figure 14:
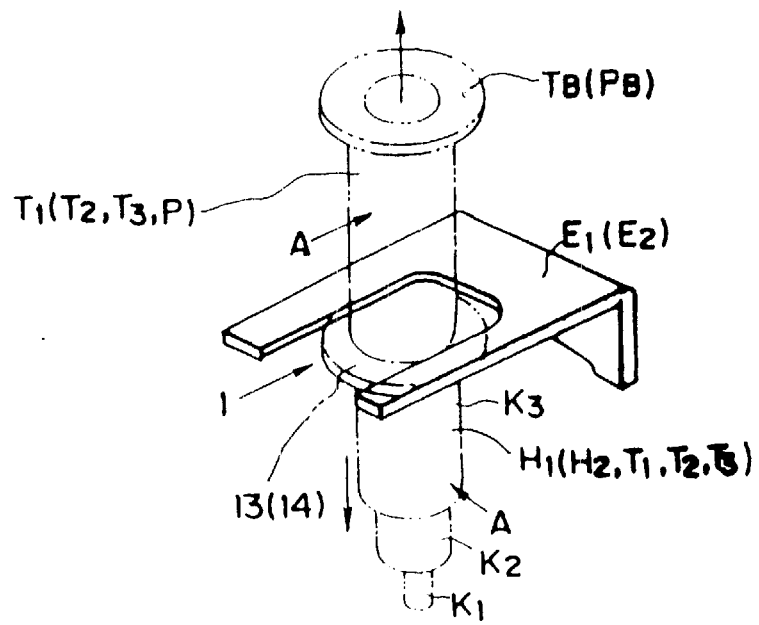
FIG. 14 is a perspective view for explanation of an example of configuration of a chip removing body.

Then the locked state of the chip $T_2$ and filter holder $H_2$ is released by the filter holder removing body $E_1$ shown in FIG. 14, and only the second filter holder $H_2$ is steeped into the cleaning liquid in the cell $C_3$ (step 11). It should be noted that the chip $T_2$ is transferred to just above the chip removing body E, removed from the pipette nozzle P, and is aborted according to the sequence described above.

It should be noted that the filter holder removing body $E_1$ has a flat surface with a notched groove 15 having a substantially U-shaped form, and a diameter of the notched groove 15 is slightly larger than an external diameter of a body section of each of the chips $T_1$, $T_2$, $T_3$, but is smaller than a diameter of the flanges 13, 14 of the filter holders $H_1$, $H_2$.

Then the pipette nozzle P is transferred, as shown in FIG. 13, to just above a chip rack with the chip supported in the erected position therein, and at the position goes downward with a third chip $T_3$ set in the first stage $P_A$ in the lower edge section of the pipette nozzle P (step 12). Also in this step, the pipette nozzle P and chip $T_3$ are locked by the hook bodies 6, 6 and the connection is maintained.

Then the pipette nozzle P with this chip $T_3$ set therein is gain transferred to just above the cell $C_3$, and goes downward at the position with the second filter holder $H_2$ locked and engaged in a lower edge section of the chip $T_3$ (step 13).

Then the pipette nozzle P starts a sucking operation, and a required quantity of a mixture liquid of a cleaning liquid and DNA is sucked. With this operation, the work of refining DNA is complete.

Figure 15:
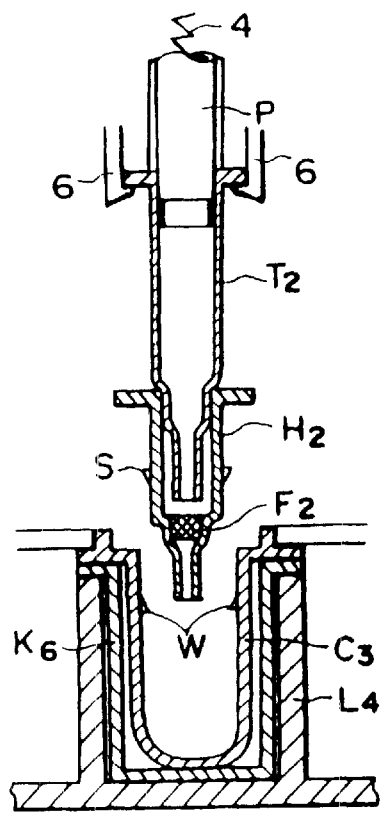
FIG. 15 is a perspective view for explanation of another example of a means for engagement between a filter holder and a cell.
Figure 16:
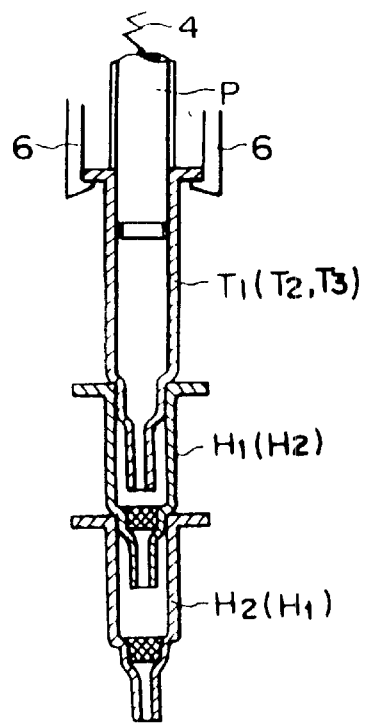
FIG. 16 is a cross-sectional view showing a case where a chip and two pieces of filter holder are connected and used in a multiple-stage form.

It should be noted that, in the present embodiment, as a means for steeping the second filter holder $H_2$ into a cleaning liquid accommodated in the cell $C_3$, for instance a locking projection W, which allows intrusion of the second filter holder $H_2$ but prevents it from going off may be provided in the cell $C_3$ in place of the removing body E as shown in FIG. 15 with also a locking projection S engaging with the locking projection W provided for the purpose to steep the second filter holder $H_2$ into a cleaning liquid accommodated in the cell $C_3$ by having the locking projection W and locking projection S engaged with each other.

Description of the embodiment shown in the figures assumes a case where a number of filter holders set in each of the chips $T_1$, $T_2$, $T_3$ is only one, but in the present invention the filter holder $H_1$ (or $H_2$) may be set in each of the chips $T_1$, $T_2$, $T_3$ with the filter holder $H_2$ (or $H_1$) set in the filter holder $H_1$ (or $H_2$) to form a two-stage joint of filter holders, and also that a number of stages may be two or more according to the necessity in the processing sequence.

Figure 17:
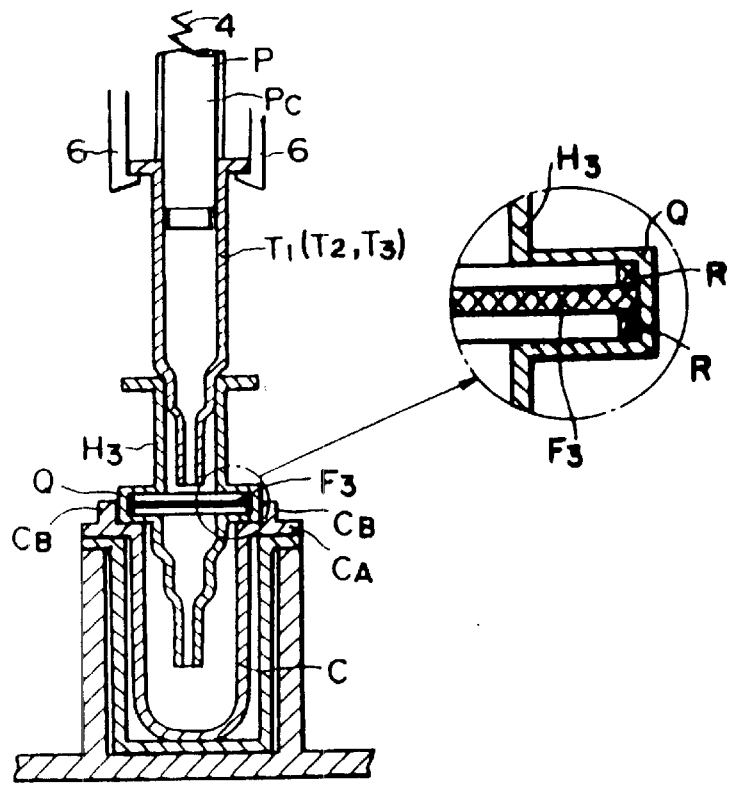
FIG. 17 is a cross-sectional view showing configuration of a filter holder with a filter having a large filter area attached thereto.

Furthermore, in certain types of liquid processing, a filter area may be short in the embodiment as shown in the figures, and in this case, as shown in FIG. 17, a filter accommodating section Q having a diameter larger than that of the body section and also having an expanding and projecting form may be provided in the intermediate section of the filter holder $H_3$ to accommodate the filter $F_3$ having a large filter area in the filter accommodating section Q. An external diameter of the filter accommodating section Q in this case should preferably be smaller than a diameter of a projections $C_B$, $C_B$ for positioning projecting from the upper edge flange section $C_A$ of the cell C. It should be noted that the sign R in the figure indicates a stay member for supporting the filter $F_3$ in an intermediate section of the filter accommodating section Q. It is needless to say that the filter $F_3$ may be supported by mesh in its lower section.

Next description is made for a step of subjecting DNA refined through the reaction steps described above to such works as extracting, recovering, isolating or amplifying with PCR or to control for temperature thereof.

Namely, in a case where such works as extracting, recovering, or isolating by making use of this pipette device with magnetic particles G with DNA or DNA-bonded substance bonded to the surface, as shown in step 14 in FIG. 13, at first the pipette nozzle P is moved upward and then transferred to just above a fourth cell $C_4$ with the second filter holder $H_2$ left in cell$_3$ via a filter holder removing body $E_2$ having the same configuration as that of the filter holder removing body $E_1$ and the sucked DNA solution is discharged into the cell $C_4$.

A required quantity of reaction liquid containing magnetic particles G with DNA or DNA-bonded substance bonded to the surface thereof has been supplied into this cell $C_4$, and when the DNA solution is discharged into the reaction liquid, a reaction between DNA fragments and the magnetic particles G is started.

The chip $T_3$ with the DNA solution having been discharged into the cell $C_4$ is removed from the lower edge section of the pipette nozzle P according to the processing sequence like in a case of the chip $T_1$ or chip $T_2$, and is aborted.

It is needless to say that then the chip $T_4$ is set in the lower edge section of the pipette nozzle P according to the processing sequence as described above.

Then, after a certain period of time has passed, the pipette nozzle P goes downward and steeps the chip $T_4$ into the reaction liquid, the magnetic body M contacts the intermediate diameter section $K_{12}$ of the chip $T_4$, the works of sucking and discharging the liquid by the pipette nozzle P is executed at least once according to the necessity, and separation between the magnetic particles and the reaction liquid is executed (step 15). Then the sucking and discharging work is executed to a slow speed so that almost all the magnetic particles are captured. In this case, it is important for completely attracting the magnetic particles to provide controls over the sucking and discharging operations so that the final liquid surface of the reaction liquid sucked or discharged passes through an area effected by a magnetic force generated by the magnetic body M.

With this separating operation, only the magnetic particles G with DNA bonded thereto are attracted almost completely onto an internal surface of the chip $T_4$, and the residual liquid is discharged into the cell $C_4$.

In this embodiment, the processing is executed by moving the magnetic body M upward and backward simultaneously in a direction perpendicular to the longitudinal direction of the chip $T_4$ or turning ON/OFF an electric magnet.

In a case where processing is executed with an electric magnet, the electric magnet is controlled so that the electric magnet is turned ON to generate a magnetic force magnet when it contacts an external surface of the chip $T_4$ and is moved upward and backward simultaneously, when degaussed, in a direction perpendicular to the longitudinal direction of the chip $T_4$.

Then this chip $T_4$ with magnetic particles G attracted onto the internal surface is transferred to a cell $T_5$ in which such a reagent as restriction enzyme liquid or the like required for extracting, recovering, and isolating the target DNA, and at the position operations for sucking or discharging the reagent such as the restriction enzyme liquid are executed by pumping as described above (step 16). The operations for sucking and discharging the reagent are executed several times continuously with a tip section of the chip $T_4$ steeped into the reagent, so that intrusion of bubbles is prevented. In this step, by setting the magnetic body M so that a magnetic force generated by the magnetic body M is not effective, works of mixing and agitating the reagent such as a restriction enzyme liquid and the magnetic particles can be executed with high precision, and an excellent reaction state can be insured.

After the reagent such as a restriction enzyme liquid and magnetic particles are fully agitated and mixed with each other, the chip $T_4$ again sucks and discharges this liquid slowly, and executes the operations once or required times according to the necessity, and separation of magnetic particles from the liquid with the magnetic body M is executed.

With the operations, only the magnetic particles G with DNA bonded thereto are almost completely attracted onto an internal surface of the chip $T_4$ and the residual liquid is discharged into the cell $C_5$ (step 17).

Then the chip $T_4$ with magnetic particles G attracted onto the internal surface thereof is transferred to cells $C_6$, $C_7$ by turns, in which a reagent required for extracting, recovering, and isolating a target DNA is previously accommodated, and at the positions where the cells $C_6$, $C_7$ are provided, and the reaction processing by pumping is executed like in the cases described above (step 18).

In this step, by setting the magnetic body M in the state wherein a magnetic force generated by the magnetic body M is not effective, works of agitating and mixing the reagent and magnetic particles G with each other can be executed with high precision. It is needless to say that times of pumping is not limited to the values employed in the above cases, and can be increased or reduced according to the necessity.

Also in a case where temperature control or amplification is required during the processing described above, if it is required to maintain the temperature at 90° C., 60° C., or 40° C., the reaction liquid may be transferred to the thermostatic cells $C_{8A}$, $C_{8B}$, $C_{8C}$ each heated to the target temperature. In this case, as compared to a case where temperature control is executed with one unit of heating means like in the conventional technology or a case where a solution is transferred vessel by vessel to the heating section, the reaction can be executed effectively, and also amplification under controlled temperature can easily be executed within a short period of time, and further a device for transferring vessels is not required, so that the apparatus can be simplified.

Figure 18:
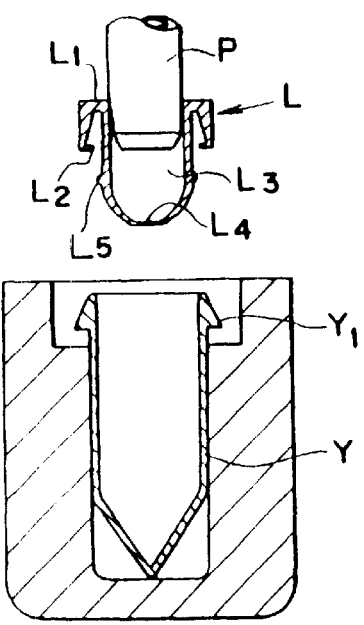
FIG. 18 is a cross-sectional view of a thermostatic vessel and a covering body used in this embodiment.
Figure 19:
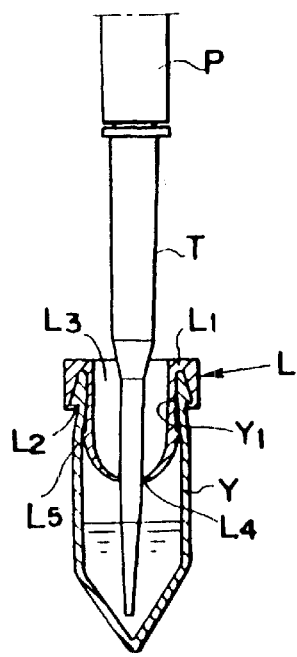
FIG. 19 is an explanatory view showing a state where a thin film body of the covering body is broken by a chip and a DNA amplifying liquid accommodated therein is sucked.

Furthermore, if a sample is to be heated to a high temperature such as 60° C. or 90° C., a mixture solution is evaporated, and to prevent the evaporation, in this embodiment, as shown in FIG. 18, it is desirable to set a covering body L.

This covering body L is engaged and locked in a thermostatic cell $C_8$ to be heated to a high temperature of the thermostatic cells $C_{8A}$, $C_{8B}$, $C_{8C}$ accommodated in a vessel accommodating hole provided in a heating member such as a heater block, and comprises a flat surface section $L_1$, having a diameter larger than a bore of the thermostatic cell $C_8$, a locking piece section $L_2$ having a substantially L-shaped form and engaging with a locking projection $Y_1$ extending downward from a periphery of this flat surface section $L_1$ and projecting to above an external periphery of the thermostatic cell $C_8$, a supporting groove $L_3$ provided in a concave form at a center of the flat surface section $L_1$, a tin film section $L_4$ closing a bottom section of the supporting groove section $L_3$ and formed with aluminum or a similar material, and a seal projecting section $L_5$ projecting from an external periphery of the supporting groove section $L_3$, and the supporting groove section $L_3$ has a bore which is identical to an outer diameter of a tip of the pipette nozzle P.

It should be noted that the thin film section $L_4$ described above may be formed by heating and welding a separate seal material such as aluminum to the supporting groove section $L_3$ or by means of supersonic welding, or may be formed with soft plastics, which is the same material as that for the supporting groove section $L_3$, into a thin film form.

For the reasons as described above, after a mixture solution is poured into the thermostatic cell $C_8$, the pipette nozzle P with the chip $T_4$ having been removed therefrom is transferred to a position where the covering body L is stocked, then goes down with the tip section of the pipette nozzle P press-fit into the supporting groove section $L_3$ of the covering body L, and the pipette nozzle P is transferred with the covering body L supported thereon to just above the thermostatic cell $C_8$, where the locking piece section $L_2$ of the covering body L is engaged with a locking projection $Y_1$ of the thermostatic cell $C_8$. It is needless to say that the thermostatic cell $C_8$ is locked so that it is not raised from a heating member such as a heater block.

After the work as described above is finished, the pipette nozzle P goes upward, and in this step, the covering body L is fixed to the thermostatic cell $C_8$ so that it is not removed from the thermostatic cell $C_8$, and for this reason the tip section of the pipette nozzle P goes out of the supporting groove section $L_3$ in the covering body L, and only the pipette nozzle P is moved to a prespecified position.

Then a new chip (not shown) is set to the tip section of the pipette nozzle P, and the pipette nozzle P is again transferred to just above the thermostatic cell $C_8$, and goes down there with the tip section of the chip T inserted into the supporting groove section $L_3$ of the covering body L and breaking through the thin film section $L_4$ downward, and then the pipette nozzle P sucks a mixture solution accommodated in the thermostatic cell $C_8$ thereinto, goes upward, and sends the sucked mixture solution to the next thermostatic cell $C_8$ or cell $C_9$.

Thus, all of the DNA solution sucked into the cell $C_7$ or the thermostatic cell $C_{8A}$ is discharged into the cell $C_9$. Then the magnetic body M contacts the intermediate diameter section $K_{12}$ of the chip $T_4$, operations for sucking and discharging by the pipette nozzle P are executed once or required times to separate the magnetic particles G from the DNA solution, and only the DNA solution is discharged with the magnetic particles G attracted onto an internal surface of the chip $T_4$ (step 19).

Figure 20:
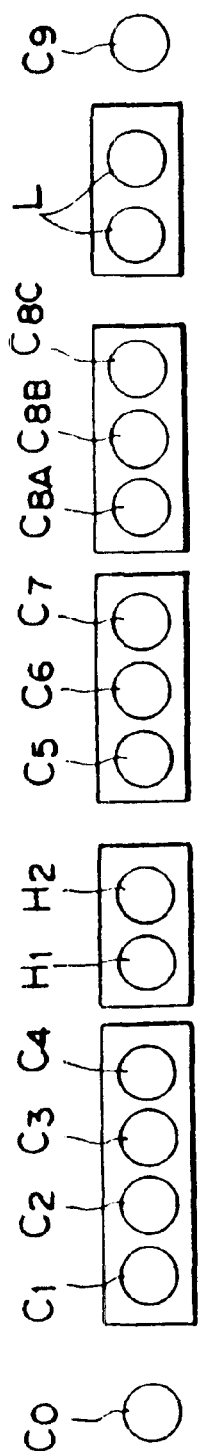
FIG. 20 is a flat view for explanation of a state where a filter holder and a cell according to this embodiment are set in a cassette for each group used in the reaction processing step.

The above description of the first embodiment of the present invention assumes a case where the filter holders $H_1$, $H_2$, sample cell $C_0$, and cells $C_1$ to cell $C_9$ are arrayed in the order of reaction steps, but the present invention is not limited to this configuration, and as shown in FIG. 20, excluding the sample cell $C_0$ and DNA recovery cell $C_9$, each of a group of cells $C_1$ to $C_4$ used for refining with a filter, a group of filter holders $H_1$, $H_2$, a group of cells $C_5$ to $C_7$ processed with the magnetic particles G, and a group of thermostatic cells $C_{8A}$ to $C_{8C}$ may be set in a cassette with the pipette nozzle P driven and controlled according to the processing sequence described above. It is needless to say that the covering body L may be provided in parallel to a cassette of the thermostatic cells $C_{8A}$ to $C_{8C}$.

Figure 21:
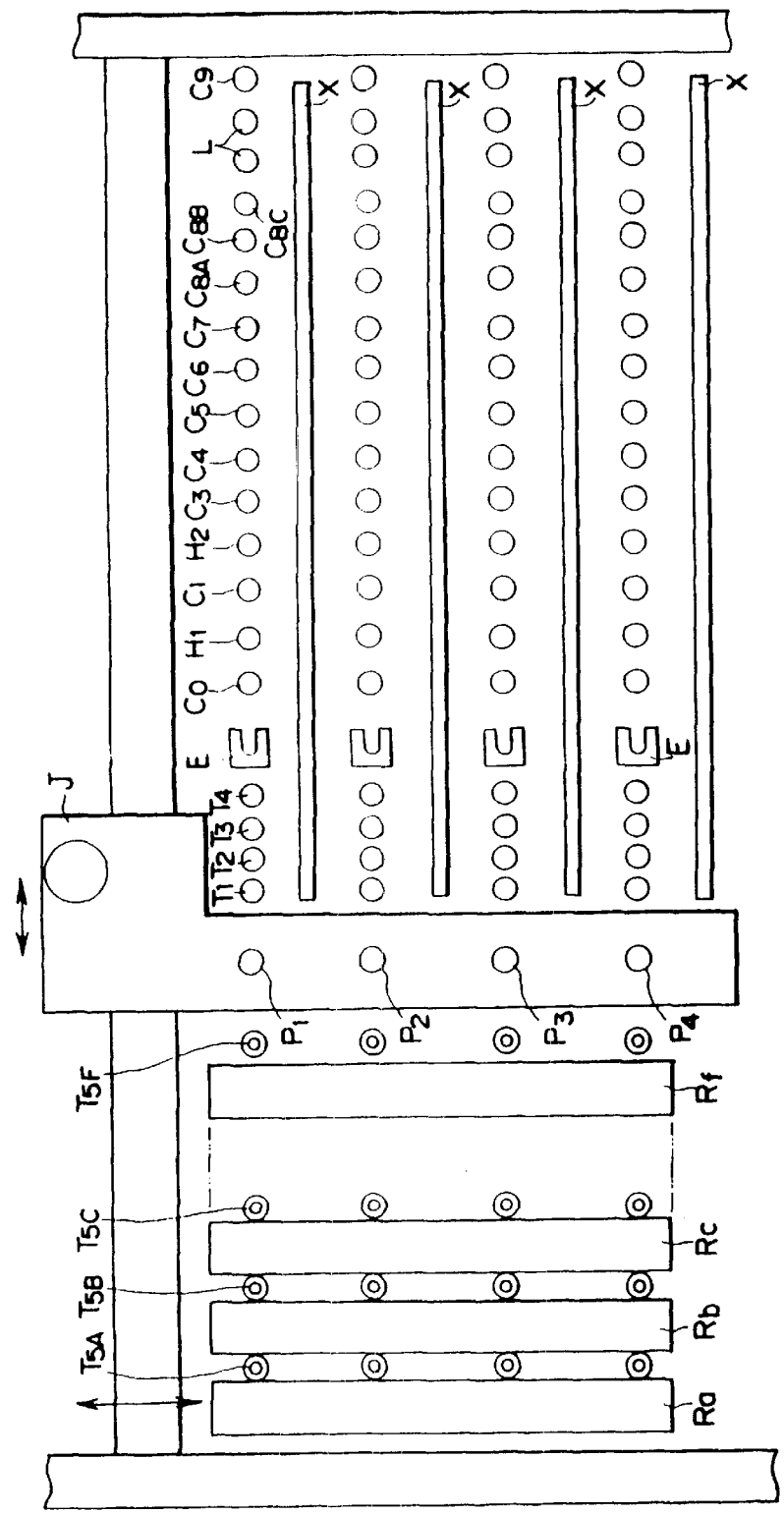
FIG. 21 is a flat view for explanation of general configuration of an apparatus for extracting, recovering, and isolating DNA comprising a plurality of reaction lines according to a second embodiment of the present invention.

FIG. 21 shows a second embodiment of the present invention, and this embodiment shows a case where a plurality of reaction lines, for instance, 4 arrays of reaction lines each having the same configuration as that of the single reaction line are provided and the lines are separated from each other with a partition wall X. It is needless to sat that, in this case, a required number of pipette nozzles are provided in series for each reaction line so that a plurality of samples can simultaneously be processed.

Also it should be noted that the reagent vessels Ra, Rb, Rc, Rd, Re, Rf arrayed along each of the reaction lines above and chips $T_{5A}$, $T_{5B}$, $T_{5C}$, $T_{5E}$, $T_{5F}$ each for pipetting each reagent are provided in parallel along the trajectories of the pipette nozzles $P_1$, $P_2$, $P_3$, $P_4$ moving along each of the reaction lines.

The partition wall X comprises a rectangular plate body having a size in a range including a tip section of each of the pipette nozzle $P_1$, $P_2$, $P_3$, $P_4$ when pulled up, and this partition wall X forms a working space separated from a neighboring reaction line, and with this construction it is possible to prevent foreign materials other than target DNA from coming in from other reaction lines.

It should be noted that an air inhalator (not shown) having a long air inhalating port in the longitudinal direction of each reaction line may be provided between each reaction line for air inhalation in place of the partition wall X.

With this construction, a curtain of a downward air flow is generated in each line, and the same working space as that formed with the partition wall X described above is formed, so that it is possible to prevent foreign materials other than the target DNA from coming in from other reaction lines without fail. In a case where an air inhalator is used, there exists no physical curtain, so that a form and movement of a pipette nozzle allowable in the production line is relatively free. Furthermore the air inhalator may be provided above each reaction line, and in this case a curtain of upward air flow is generated between the reaction lines, and a similar working space is generated between each line. It is needless to say that this air inhalating method may be use in combination with the partition wall X described above, and in that case cross contamination between the reaction lines can be prevented with higher accuracy.

Figure 22:
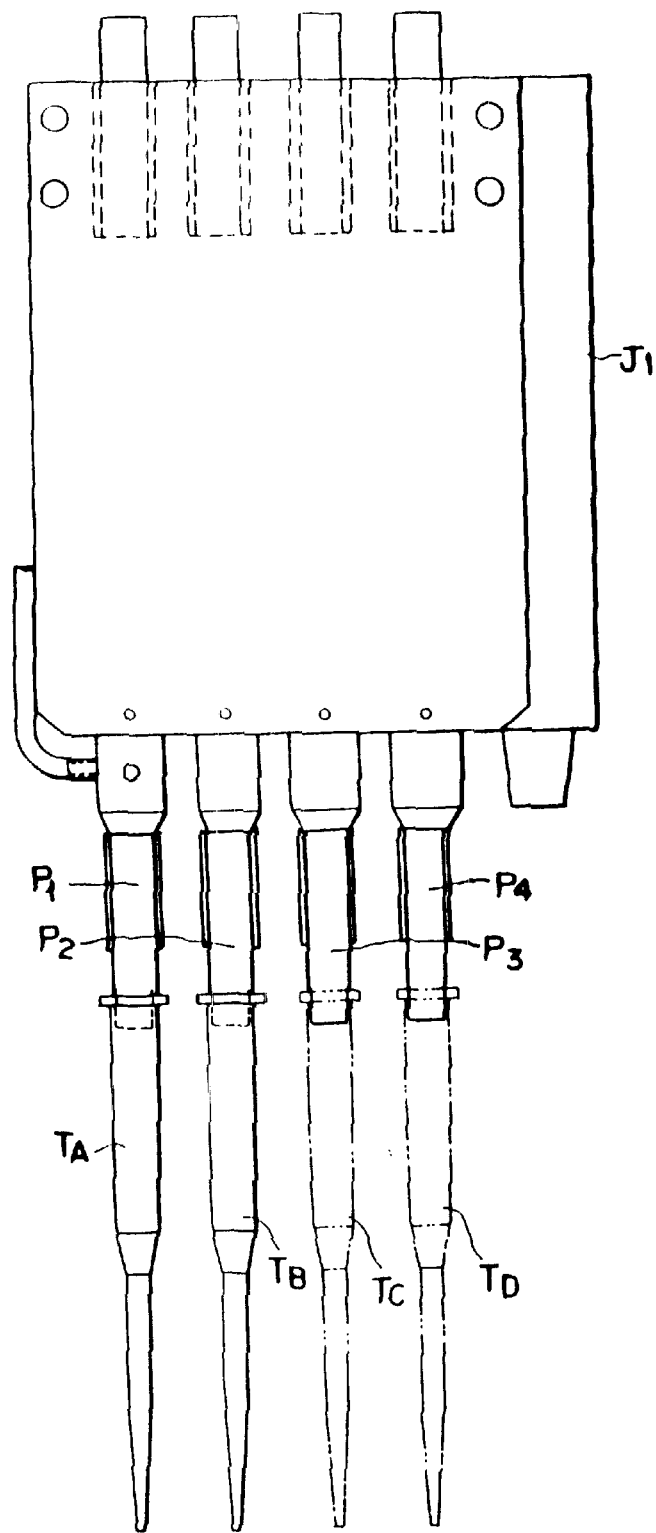
FIG. 22 is a front view showing a quadrupled nozzle cylinder applicable to the present invention.

FIG. 22 shows a cylinder $J_1$ used in the second embodiment of the present invention, and this cylinder $J_1$ shows the configuration in a case where works in each reaction line are not executed with separate cylinders, but executed only with this cylinder $J_1$, and the configuration and effects thereof are similar to those provided by this type of cylinder known in the conventional technology excluding the point that four chips $T_1$, $T_2$, $T_3$, $T_4$ or $T_{5A}$, $T_{5B}$, $T_{5C}$, $T_{5E}$ or the like used in the second embodiment above each detachably set in the pipette nozzles $P_1$, $P_2$, $P_3$, $P_4$ respectively can simultaneously be set, and detailed description thereof is omitted herein. A number of chips used in the present invention is not limited to four, and a plurality of chips may be set according to a number of liquid processing lines.

Figure 23:
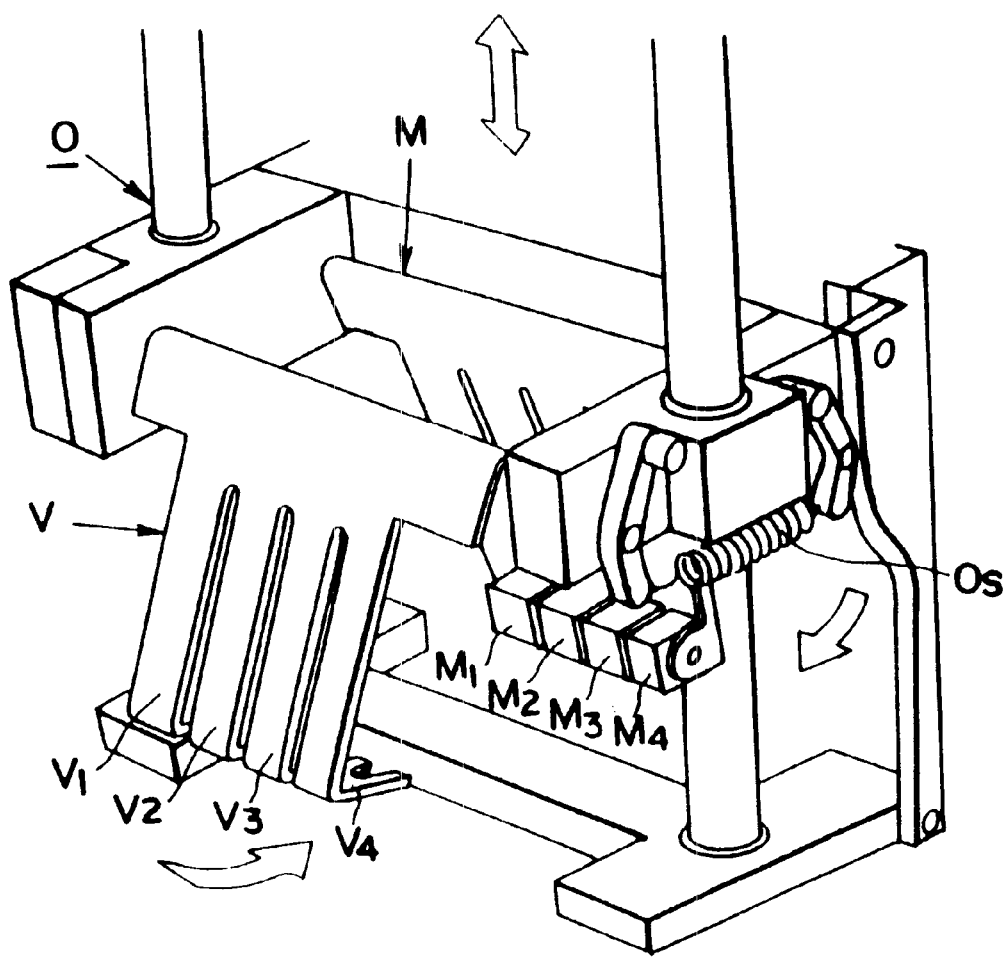
FIG. 23 is a perspective view showing an example of configuration of a holding body and a magnetic body used in processing with the four-stage nozzle cylinder.
Figure 24:
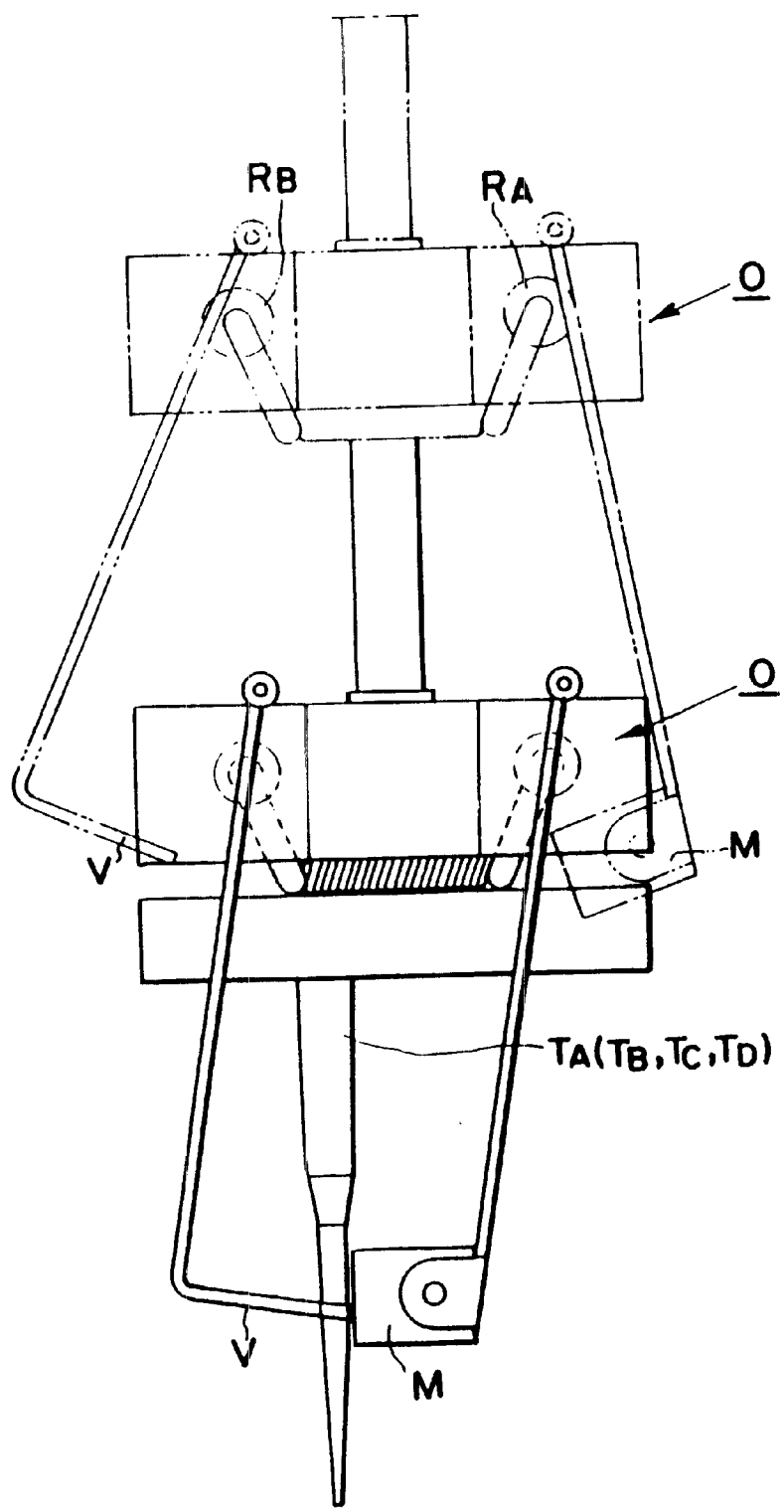
FIG. 24 is an explanatory view for operations of the holding body as well as of the magnetic body.

FIG. 23 and FIG. 24 show a mechanism suited to driving and controlling a magnetic body M and a holding body V when a liquid is processed with the cylinder shown in FIG. 22, and in this instance a magnetic body M having magnetic sections $M_1$, $M_2$, $M_3$, $M_4$ formed into a shape like comb teeth and a holding body V having holding sections $V_1$, $V_2$, $V_3$, $V_4$ also formed into a shape like comb teeth are pivotally supported by an up-down mechanism O in a state where opening or closing thereof is freely executed, and this up-down mechanism O is moved upward and downward, when rollers $O_R$, $O_R$ of the up-down mechanism O are closed as shown in FIG. 24. The magnetic body M and holding body V are moved and closed by the spring $O_S$ shown in FIG. 23 to hold a chip between them, and as a result the magnetic body M is simultaneously contacted to the four chips $T_A$, $T_B$, $T_C$, and $T_D$, or each chip is simultaneously held by the holding body V and the magnetic body M.

The embodiment shown in FIG. 23 and FIG. 24 shows a case where a plurality of liquid processing lines are formed with partition lines like in the second embodiment by providing the magnet body M and the holding body V, and in this case the magnetic body M and holding body V never collide against the partition wall, and such works as attracting, agitating, and mixing magnetic particles or sucking and discharging a liquid can simultaneously be executed in four liquid processing lines at the same timing, so that the processing efficiency can substantially be improved with simple configuration. It is needless to say that the present invention is not limited to a case where four pieces of magnetic body M and four holding bodies V are used like in the embodiment described above, and that any number of magnetic bodied and holding bodies may be used according to the necessity.

Also it should be noted that a filter may be set above a large diameter section of each chip to prevent a liquid from being deposited on or attracted to the sucking/discharging line.

INDUSTRIAL APPLICABILITY

As described above, the liquid processing method and the apparatus for the same making use of the pipette device according to the present invention is suited for executing such works as quantifying, separating, taking out, pipetting, cleaning, condensing, and diluting a liquid or a target high molecular substance contained in a liquid as well as such works as extracting, recovering, and isolating the target high molecular substance automatically and with high precision by means of sucking and discharging the liquid with a liquid sucking/discharging line in the pipette device. The liquid processing method and the apparatus for the same described above is suited for, for instance, executing such works as quantifying, separating, taking out, pipetting, clarifying, condensing, diluting a useful substance such as antibiotics, a genetic substance such as DNA or an immunological substance such as antibodies, and/or such works as extracting, recovering, and isolating a target high molecular substance automatically and with high precision by means of sucking and discharging the liquid in the liquid sucking/discharging line in the pipette device.

What is claimed is:

1. A liquid processing method making use of a pipette device which sucks a liquid containing a target high molecular substance selected from the group consisting of molecular level organisms, microorganisms, cellular substances, and bacteria, via a tip detachably set in a sucking port or a discharging port of a liquid sucking/discharging line from inside of a vessel and transfers the liquid or the target high molecular substance to a target next processing position, wherein said tip comprises a small diameter section steeped into a liquid, a large diameter section having a capacity larger than a capacity of a vessel in which a liquid is accommodated, and an intermediate section provided between the small diameter section and the large diameter section and having a diameter smaller at least than that of the large diameter section, comprising the steps of:

sucking a liquid containing the target high molecular substance from the vessel via the tip into the large diameter section in such a manner that a final liquid surface of the liquid passing through said tip always reaches a substantially central portion of the intermediate section, separating the target substance by a means selected from the group consisting of a means using magnetic particles for absorbing or bonding to the target substance and captured at the intermediate section with the magnetic field removably applied by a magnetic body provided in only the substantially central portion of the intermediate section outside of the tip and a means using a filter set, and transferring the liquid or the target substance to the target next processing position.

2. A liquid processing method making use of a pipette device according to claim 1, wherein in the step for separating, an internal diameter of the intermediate section of said tip has a dimension appropriate for a ferromagnetic field of said magnetic body to provide effects therein, and magnetic particles are captured due to a magnetic force to provide effects therein, and magnetic particles are captured due to a magnetic force generated in the ferromagnetic field of the magnetic body within a short period of time.

3. A liquid processing method making use of a pipette device according to claim 1, wherein in the step for separating, an internal diameter of the intermediate section of said tip is formed so as to have the substantially same width dimension as that of a contacting surface of a magnetic body contacting said intermediate section.

4. A liquid processing method comprising using a pipette device which sucks a liquid containing a target high molecular substance via a smaller diameter section immersed in a liquid, of a hollow cylinder detachably set in a sucking port or a discharging port of a liquid sucking/discharging line from inside of a vessel to a larger diameter section thereof having a capacity larger than a capacity of a vessel in which a liquid is accommodated, and via an intermediate section of the hollow cylinder provided between the smaller diameter section and the larger diameter section and having a diameter smaller than at least that of the larger diameter section, in such a manner that a final liquid surface of the liquid passing through the hollow cylinder always reaches a substantially central portion of the intermediate section, and then transfers the liquid containing the target high molecular substance to a target substance processing position, comprising the steps of:

adhering the magnetic particles absorbing or bonding to said sucked target high molecular substances onto an inner wall of the intermediate section of said hollow cylinder and separating the high molecular substance, by means of a magnetic force removably applied externally to only the substantially central portion of the intermediate section of said cylinder, performing steps selected from the group consisting of capturing, extracting, isolating, amplifying, labeling, and measuring said target high molecular substance only with a cylinder positioned in said liquid sucking/discharging line, a magnetic force, and at least one type of magnetic particles.

5. A liquid processing method according to claim 4, wherein said target high molecular substance is an antibiotic, a genetic material substance, an immunological substance, or a physiologically active substance.

6. A liquid processing method according to claim 4, wherein by causing the cylinder positioned in said liquid sucking/discharging line to react with magnetic particles, a refining process such as capturing cells, having cell cores of protein lysed is performed, and a particular target high molecular substance is extracted.

7. A liquid processing method according to claim 4, wherein by using magnetic particles with a probe or biotin or streptoavidin coated thereon, a particular base sequence segment is isolated.

8. A liquid processing method according to claim 4, wherein by causing the cylinder positioned in said liquid sucking/discharging line to react with magnetic particles, a refining processing is performed whereby a particular target high molecular substance is extracted and then a particular base sequence piece is isolated with another type of magnetic particles with a probe or biotin or streptoavidin coated thereon.

9. A liquid processing method according to claim 4, wherein after a series of steps selected from the group consisting of capturing, extracting, and isolating a target high molecular substance by using said magnetic particles, by making an isolated particular base sequence piece emit light through chemical luminescence, fluorescence and enzymatic coloration, the presence or a quantity of the particular base sequence piece is detected and/or measured.

10. A liquid processing method according to claim 4, wherein by causing the cylinder positioned in said liquid sucking/discharging line to react with magnetic particles, a refining process is performed whereby a particular target high molecular substance is extracted, the extracted target high molecular substance is amplified, a particular base sequence piece is isolated with another type of magnetic particles with a probe or biotin or streptoavidin coated thereon and then the presence of or the amount of a particular base sequence segment is detected and measured by causing the isolated piece to emit light through chemical luminescence, fluorescence, or enzymatic coloration.

11. A liquid processing method comprising using a pipette device which sucks a liquid containing a target high molecular substance via a smaller diameter section immersed in a liquid of a hollow cylinder detachably set in a sucking port or a discharging port of a liquid sucking/discharging line from inside of a vessel to a larger diameter section thereof having a capacity larger than a capacity of a vessel in which a liquid is accommodated, and via an intermediate diameter section of the hollow cylinder provided between the smaller diameter section and the larger diameter section and having a diameter smaller than at least that of the larger diameter section, in such a manner that a final liquid surface of the liquid passing through the hollow cylinder always reaches a substantially central portion of the intermediate section, and then transfers the liquid containing the target high molecular substance to a target substance processing position, comprising the steps of:

adhering the magnetic particles absorbing or bonding to said sucked target high molecular substance, onto an inner wall of the intermediate section of said hollow cylinder and separating the target high molecular substance by a means selected from the group consisting of a means using a magnetic force removably applied externally to only the substantially central portion of the intermediate section of said cylinder and a means using a filter set, and the steps of separating, taking out, pipetting, clarifying, condensing, diluting said target high molecular substance and/or steps for capturing, extracting, isolating, amplifying, labeling, and measuring the substance are performed in a single liquid sucking/discharging line, wherein working spaces in the single liquid sucking/discharging line are separated from each other.

12. A liquid processing method according to claim 11, wherein the working spaces are separated from each other with partitions.

13. A liquid processing method according to claim 12, wherein working spaces in said single liquid sucking/discharging line are separated from each other with partitions, and air in the working spaces separated from each other with the partitions is sucked from an air sucking port provided in the working space.

14. A liquid processing method according to claim 11, wherein air sucking ports are provided in each line working space in said single liquid sucking/discharging line, and the working spaces are separated from each other with an air flow.

15. A liquid processing method according to claim 11, wherein said target high molecular substance is an antibiotic, a genetic material substance, an immunological substance, or a physiologically active substance.

16. A liquid processing method according to claim 11, wherein said plurality of liquid sucking/discharging lines perform the steps of separating, taking out, pipetting, clarifying, condensing, diluting said target high molecular substance and/or the steps of capturing, extracting, isolating, amplifying, labeling, and measuring the substance in each line according to the same timing.

17. A liquid processing method according to claim 11, wherein said plurality of liquid sucking/discharging lines perform the operations of sucking and discharging each liquid by a different timing according to a processing step specified by each liquid.

18. A liquid processing method comprising using a pipette device which sucks a liquid containing a target high molecular substance via a smaller diameter section immersed in a liquid, of a hollow cylinder detachably set in a sucking port or a discharging port of a liquid sucking/discharging line from inside of a vessel to a larger diameter section thereof having a capacity larger than a capacity of a vessel in which a liquid is accommodated, and via an intermediate diameter section of the hollow cylinder provided between the smaller diameter section and the larger diameter section and having a diameter smaller than at least that of the larger diameter section, in such a manner that a final liquid surface of the liquid passing through the hollow cylinder always reaches a substantially central portion of the intermediate section, and then transfers the liquid containing the target high molecular substance to a target substance processing position, comprising the steps of:

adhering the magnetic particles absorbing or bonding to said target high molecular substance onto an inner wall of the intermediate section of said cylinder by means of a magnetic force removably applied externally to only the substantially central portion of the intermediate section of said cylinder, agitating and mixing magnetic particles absorbed in said cylinder with a reagent or cleaning water, under conditions in which the steps of sucking and discharging liquid are continuously executed in the liquid sucking/discharging line and for times sufficient to agitate and mix the liquid with the magnetic particles, and controlling the temperature required for said target high molecular substance, reaction of said reagent or amplification of the target high molecular substance by transferring the reaction liquid or a liquid to be amplified into a thermostatic vessel maintaining said cylinder at a constant temperature.

19. A liquid processing method according to claim 18, wherein said target high molecular substance is an antibiotic, a genetic material substance, an immunological substance, or a physiologically active substance.

20. A liquid processing method according to claim 18, wherein, when controlling a temperature in the thermostatic vessel, a cover is placed over a tip section of said liquid sucking/discharging line, and said cover is placed via the liquid sucking/discharging line on the thermostatic vessel.

21. A liquid processing method according to claim 20, wherein said liquid sucking/discharging line or a cylinder positioned in said line is driven and controlled so that said cover is seized and broken and a reaction liquid or a liquid to be amplified in a thermostatic vessel is sucked thereby.

22. A liquid processing method comprising using a pipette device which sucks a liquid containing a target high molecular substance via a smaller diameter section immersed in a liquid, of a hollow cylinder detachably set in a sucking port or a discharging port of a liquid sucking/discharging line from inside of a vessel to a larger diameter section thereof having a capacity larger than a capacity of a vessel in which a liquid is accommodated, and via an intermediate diameter section of the hollow cylinder provided between the smaller diameter section and the larger diameter section and having a diameter smaller than at least that of the larger diameter section, in such a manner that a final liquid surface of the liquid passing through the hollow cylinder always reaches a substantially central portion of the intermediate section, and then transfers the liquid containing the target high molecular substance to a target substance processing position, comprising the steps of:

adhering the magnetic particles absorbing or bonding to said target high molecular substance onto an inner wall of the liquid passing section of said hollow cylinder and separating the target high molecular substance by a means selected from the group consisting of a magnetic force removably applied externally to only the substantially central portion of the intermediate section of said cylinder and a filter set, and controlling the sucking/discharging in said hollow cylinder.

23. A liquid processing method according to claim 22, wherein sucking or discharging of the liquid is controlled so that absorption of magnetic particles onto an internal surface of a cylinder positioned in said liquid sucking/discharging line is performed by passing a solution containing magnetic particles through a magnetic field inside the cylinder at a slow speed appropriate for complete capture of the magnetic particles.

24. A liquid processing method according to claim 22, wherein controls are provided so that the final liquid surface of a liquid passing through said cylinder when sucked into or discharged from the cylinder is always subjected to said magnetic force.

25. A liquid processing method according to claim 22, wherein, when sucking magnetic particles into said cylinder, a tip section of a cylinder positioned in the liquid sucking/discharging line is driven and controlled so that it contacts the inside bottom surface of the vessel containing the liquid therein and then is slightly raised therefrom so as to suck the liquid.

26. A liquid processing method according to claim 22, wherein agitation and mixing of magnetic particles absorbed in said cylinder with a reagent or clarifying water is achieved under conditions in which the steps of sucking and discharging the liquid are continuously executed in the liquid sucking/discharging line and for times sufficient to agitate and mix the liquid with the magnetic particles.

27. A liquid processing method according to claim 22, wherein said target high molecular substance is an antibiotic, a genetic material substance, an immunological substance, or a physiologically active substance.

* * * * *